United States Patent
Lo et al.

(10) Patent No.: US 9,348,975 B2
(45) Date of Patent: May 24, 2016

(54) OPTIMIZING THERAPY OUTCOMES FOR PERITONEAL DIALYSIS

(75) Inventors: Ying-Cheng Lo, Green Oaks, IL (US); Alp Akonur, Evanston, IL (US); Isaac Martis, Chicago, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 267 days.

(21) Appl. No.: 12/431,458

(22) Filed: Apr. 28, 2009

(65) Prior Publication Data

US 2009/0275881 A1 Nov. 5, 2009

Related U.S. Application Data

(60) Provisional application No. 61/050,114, filed on May 2, 2008.

(51) Int. Cl.
*G06F 19/00* (2011.01)
*A61M 1/28* (2006.01)

(52) U.S. Cl.
CPC ............ *G06F 19/3481* (2013.01); *A61M 1/28* (2013.01); *A61M 1/281* (2014.02);
(Continued)

(58) Field of Classification Search
CPC ....... A61M 1/28; A61M 1/284; A61M 1/287; A61M 2205/50; A61M 2205/505; A61M 2205/52; A61M 1/14; A61M 1/1613; A61M 1/1654; A61M 2230/201; A61M 1/1647; A61M 1/1696; A61M 1/3479; A61M 1/281; A61M 2205/3569; A61M 2205/6018; A61M 2205/6054; A61M 2205/6072; G06F 19/323; G06F 19/3468; G06F 19/3481

USPC ............. 604/29, 28, 5.01, 5.04, 27; 600/300, 600/587; 703/2; 700/100
See application file for complete search history.

(56) References Cited

U.S. PATENT DOCUMENTS 3,447,161 A 6/1969 Weikel
3,468,447 A 9/1969 Smalley
(Continued)

FOREIGN PATENT DOCUMENTS

CA 1256343 6/1989
DE 390140 2/1924
(Continued)

OTHER PUBLICATIONS

Written Opinion and International Search Report For Corresponding International Application No. PCT/US2009/042106 dated Aug. 25, 2009.
(Continued)

*Primary Examiner* — Kami A Bosworth
*Assistant Examiner* — Brandy S Lee
(74) *Attorney, Agent, or Firm* — K&L Gates LLP

(57) ABSTRACT

Peritoneal dialysis therapy outcomes have been calculated for a variety of dwell times of peritoneal dialysis fluids in the peritoneal cavities of dialysis patients using kinetic modeling. The length of dwell time should not be the same for every patient, but should vary according to the patient condition and needs. Some patients have a potential for expressing greater ultrafiltrate into the dialysis fluid, and these patients can benefit from a longer dwell time, whereas other patients with less potential will not benefit from a longer dwell time. An optimal or peak time is observed for each peritoneal dialysis therapy outcome, such as ultrafiltrate volume rate, urea clearance (Kt/V), and creatinine clearance, while minimizing hydrocarbon absorption. These values and input parameters can be used to tailor the peritoneal dialysis dwell time for each patient, estimating the peak dwell time that will yield the best therapy outcome for each patient.

22 Claims, 12 Drawing Sheets

(52) U.S. Cl.
CPC ... *A61M 2205/3569* (2013.01); *A61M 2205/52* (2013.01); *A61M 2205/6018* (2013.01); *A61M 2205/6054* (2013.01); *A61M 2205/6072* (2013.01)

(56) References Cited

U.S. PATENT DOCUMENTS

| | | |
|---|---|---|
| 3,858,580 A | 1/1975 | Ogle |
| 3,986,508 A | 10/1976 | Barrington |
| 4,201,208 A | 5/1980 | Cambio, Jr. |
| 4,334,551 A | 6/1982 | Pfister |
| 4,354,490 A | 10/1982 | Rogers |
| 4,432,764 A | 2/1984 | Lopez |
| 4,432,766 A | 2/1984 | Bellotti et al. |
| 4,457,749 A | 7/1984 | Bellotti et al. |
| 4,503,333 A | 3/1985 | Kulin et al. |
| 4,511,359 A | 4/1985 | Vaillancourt |
| 4,526,572 A | 7/1985 | Donnan et al. |
| 4,551,146 A | 11/1985 | Rogers |
| 4,580,816 A | 4/1986 | Campbell et al. |
| 4,610,469 A | 9/1986 | Wolff-Mooij |
| 4,623,327 A | 11/1986 | Mahurkar |
| 4,624,664 A | 11/1986 | Peluso et al. |
| 4,655,762 A | 4/1987 | Rogers |
| 4,675,004 A | 6/1987 | Hadford et al. |
| 4,701,159 A | 10/1987 | Brown et al. |
| 4,770,652 A | 9/1988 | Mahurkar |
| 4,810,241 A | 3/1989 | Rogers |
| 4,816,221 A | 3/1989 | Harvey et al. |
| 4,842,582 A | 6/1989 | Mahurkar |
| 4,895,570 A | 1/1990 | Larkin |
| 4,941,517 A | 7/1990 | Galloway |
| 4,976,683 A | 12/1990 | Gauthier et al. |
| 4,983,161 A | 1/1991 | Dadson et al. |
| 4,985,034 A | 1/1991 | Lipton |
| 5,009,636 A | 4/1991 | Wortley et al. |
| 5,100,394 A | 3/1992 | Dudar et al. |
| 5,137,524 A | 8/1992 | Lynn et al. |
| 5,158,538 A | 10/1992 | Shaw |
| 5,188,593 A | 2/1993 | Martin |
| 5,190,534 A | 3/1993 | Kendell |
| 5,211,638 A | 5/1993 | Dudar et al. |
| 5,242,425 A | 9/1993 | White et al. |
| 5,263,930 A | 11/1993 | Ensminger |
| 5,269,764 A | 12/1993 | Vetter et al. |
| 5,279,605 A | 1/1994 | Karrasch et al. |
| 5,324,128 A | 6/1994 | Gueret |
| 5,324,422 A | 6/1994 | Colleran et al. |
| 5,350,357 A | 9/1994 | Kamen et al. |
| 5,372,147 A | 12/1994 | Lathrop, Jr. et al. |
| 5,378,230 A | 1/1995 | Mahurkar |
| 5,393,101 A | 2/1995 | Matkovich |
| 5,421,823 A | 6/1995 | Kamen et al. |
| 5,431,280 A | 7/1995 | Bryant |
| 5,431,626 A | 7/1995 | Bryant et al. |
| 5,437,650 A | 8/1995 | Larkin et al. |
| 5,438,510 A | 8/1995 | Bryant et al. |
| 5,445,610 A | 8/1995 | Evert |
| 5,456,675 A | 10/1995 | Wolbring et al. |
| 5,474,683 A | 12/1995 | Bryant et al. |
| 5,489,278 A | 2/1996 | Abrahamson |
| 5,501,676 A | 3/1996 | Niedospial et al. |
| 5,507,733 A | 4/1996 | Larkin et al. |
| 5,555,897 A | 9/1996 | Lathrop, Jr. et al. |
| 5,571,093 A | 11/1996 | Cruz et al. |
| 5,582,600 A | 12/1996 | Loh |
| 5,617,012 A | 4/1997 | Murakami |
| 5,620,427 A | 4/1997 | Werschmidt et al. |
| 5,628,908 A | 5/1997 | Kamen et al. |
| 5,634,896 A | 6/1997 | Bryant et al. |
| 5,670,057 A * | 9/1997 | Chen et al. ............ 210/739 |
| 5,694,978 A | 12/1997 | Heilmann et al. |
| 5,722,947 A | 3/1998 | Jeppsson et al. |
| 5,743,892 A | 4/1998 | Loh et al. |
| 5,776,116 A | 7/1998 | Lopez et al. |
| 5,782,808 A | 7/1998 | Folden |
| 5,827,820 A | 10/1998 | duMoulin et al. |
| 5,843,474 A | 12/1998 | Williams |
| 5,863,421 A | 1/1999 | Peter et al. |
| 5,902,336 A | 5/1999 | Mishkin |
| 5,938,634 A | 8/1999 | Packard |
| 5,989,423 A | 11/1999 | Kamen et al. |
| 6,027,489 A | 2/2000 | Galato |
| 6,074,359 A | 6/2000 | Keshaviah et al. |
| 6,079,432 A | 6/2000 | Paradis |
| 6,096,011 A | 8/2000 | Trombley, III et al. |
| 6,105,770 A | 8/2000 | Vasudeva |
| 6,117,122 A | 9/2000 | Din et al. |
| 6,153,102 A * | 11/2000 | Kenley et al. ............ 210/636 |
| 6,183,465 B1 | 2/2001 | Meier et al. |
| 6,183,467 B1 | 2/2001 | Shapeton et al. |
| 6,228,047 B1 * | 5/2001 | Dadson ............ 604/29 |
| 6,232,286 B1 | 5/2001 | Goodearl et al. |
| 6,234,992 B1 | 5/2001 | Haight et al. |
| 6,358,241 B1 | 3/2002 | Shapeton et al. |
| 6,367,640 B1 | 4/2002 | Julian |
| 6,497,676 B1 | 12/2002 | Childers et al. |
| 6,558,667 B2 | 5/2003 | Nakanishi |
| 6,585,677 B2 | 7/2003 | Cowan, Jr. et al. |
| 6,592,542 B2 | 7/2003 | Childers et al. |
| 6,595,948 B2 | 7/2003 | Suzuki et al. |
| 6,814,547 B2 | 11/2004 | Childers et al. |
| 6,932,787 B2 | 8/2005 | Cowan et al. |
| 7,107,837 B2 | 9/2006 | Lauman et al. |
| 7,153,286 B2 | 12/2006 | Busby et al. |
| 7,208,092 B2 | 4/2007 | Micheli |
| 7,297,689 B2 | 11/2007 | Miyata |
| 7,303,541 B2 | 12/2007 | Hamada et al. |
| 7,354,417 B1 | 4/2008 | Levin et al. |
| 7,421,316 B2 | 9/2008 | Gray et al. |
| 7,507,219 B2 | 3/2009 | Noack |
| 7,507,220 B2 | 3/2009 | Childers et al. |
| 7,618,392 B2 | 11/2009 | Martis et al. |
| 2001/0040127 A1 | 11/2001 | Donig et al. |
| 2002/0010437 A1 | 1/2002 | Lopez et al. |
| 2003/0006610 A1 | 1/2003 | Werth |
| 2003/0184090 A1 | 10/2003 | Guala |
| 2004/0019320 A1 * | 1/2004 | Childers et al. ............ 604/29 |
| 2004/0087986 A1 | 5/2004 | Ott |
| 2004/0111078 A1 | 6/2004 | Miyahara |
| 2004/0111293 A1 | 6/2004 | Firanek et al. |
| 2004/0111294 A1 | 6/2004 | McNally et al. |
| 2004/0238776 A1 | 12/2004 | Peters et al. |
| 2005/0089994 A1 | 4/2005 | Neftel |
| 2007/0106247 A1 | 5/2007 | Burnett et al. |
| 2008/0097283 A1 | 4/2008 | Plahey |
| 2008/0183126 A1 | 7/2008 | Landherr et al. |
| 2008/0183127 A1 | 7/2008 | Landherr et al. |
| 2008/0243211 A1 | 10/2008 | Cartwright et al. |
| 2009/0076856 A1 | 3/2009 | Darby et al. |
| 2009/0187139 A1 | 7/2009 | Mastalli et al. |
| 2009/0222119 A1 | 9/2009 | Plahey et al. |
| 2009/0271119 A1 | 10/2009 | Hamada et al. |
| 2009/0275881 A1 | 11/2009 | Lo et al. |
| 2009/0275883 A1 | 11/2009 | Chapman et al. |
| 2009/0294339 A1 | 12/2009 | Biewer et al. |
| 2009/0299273 A1 | 12/2009 | Lee et al. |
| 2010/0010423 A1 | 1/2010 | Yu et al. |
| 2010/0010426 A1 | 1/2010 | Childers et al. |
| 2010/0010427 A1 | 1/2010 | Yu et al. |
| 2010/0010428 A1 | 1/2010 | Yu et al. |

FOREIGN PATENT DOCUMENTS

| | | |
|---|---|---|
| EP | 0133020 | 2/1985 |
| EP | 0554722 | 8/1993 |
| EP | 0896827 | 2/1999 |
| EP | 1243280 | 9/2002 |
| EP | 0092528 | 3/2003 |
| EP | 1 623 731 | 2/2006 |
| EP | 1623731 | 2/2006 |
| EP | 1623731 A1 * | 2/2006 |
| EP | 1623731 | 8/2006 |
| EP | 1 872 814 | 1/2008 |

(56) References Cited

FOREIGN PATENT DOCUMENTS

| | | |
|---|---|---|
| EP | 1872814 | 1/2008 |
| GB | 894854 | 4/1962 |
| GB | 927151 | 5/1963 |
| GB | 2067075 | 7/1981 |
| GB | 2343723 | 5/2005 |
| JP | 9192216 | 7/1997 |
| JP | 10248924 | 9/1998 |
| JP | 11057419 | 3/1999 |
| JP | 11128359 | 5/1999 |
| JP | 2000014772 | 1/2000 |
| JP | 200140099 | 5/2000 |
| WO | WO 97/00095 | 1/1997 |
| WO | WO 97/35634 | 10/1997 |
| WO | 03/099355 | 12/2003 |
| WO | WO 03/099355 | 12/2003 |
| WO | 2008/027967 | 3/2008 |
| WO | WO 2008/027967 | 3/2008 |

OTHER PUBLICATIONS

Written Opinion and International Search Report For Corresponding International Application No. PCT/US2009/042103 dated Aug. 25, 2009.
Rippe B. et al. Computer Simulation of Peritoneal Fluid Transport in CAPD. Kidney International, vol. 40 (1991), pp. 315-325.
Vonesh E. F. and Rippe B., Net fluid absorption under membrane transport models of peritoneal dialysis, Blood Purif 1992; 10:209-226.
International Search Report, PCT/US2009/042103.
International Search Report, PCT/US2009/042106.
European Office Action dated Oct. 30, 2012 corresponding to European Patent Application No. 09739681.6.
Non-Final Office Action issued Jan. 7, 2010 for related U.S. Appl. No. 12/431,479.
Final Office Action issued Jun. 23, 2010 for related U.S. Appl. No. 12/431,479.
Non-Final Office Action issued Jun. 16, 2014 for related U.S. Appl. No. 12/431,479.

* cited by examiner

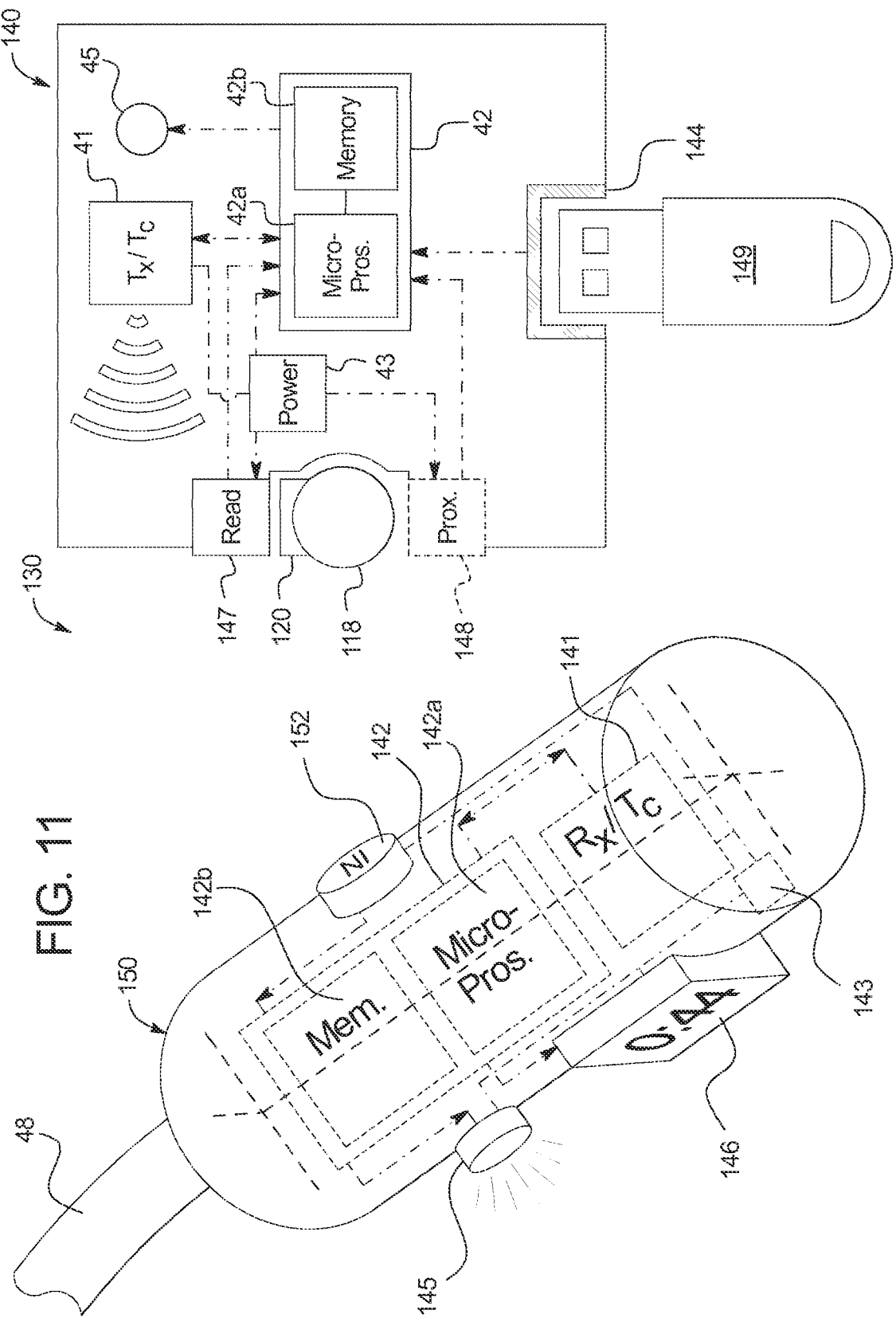

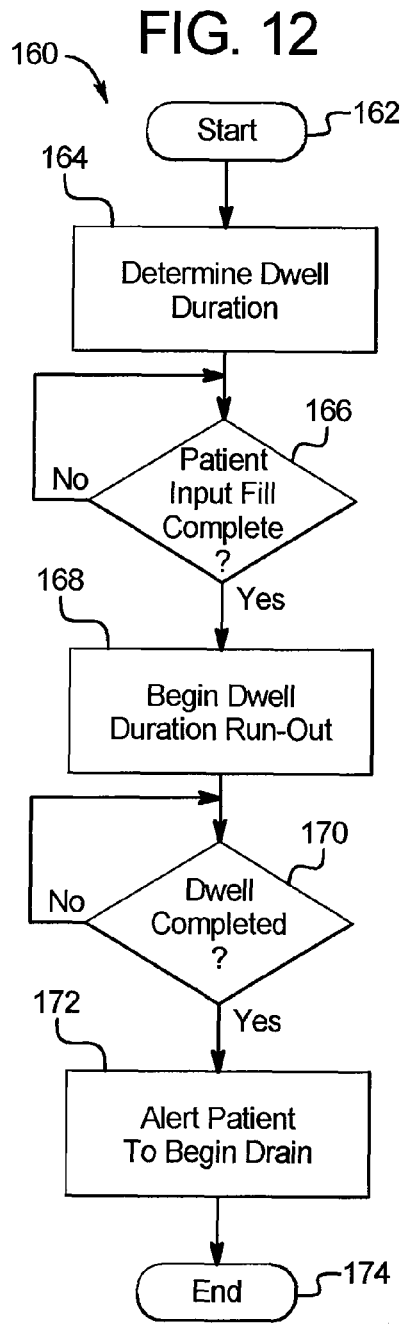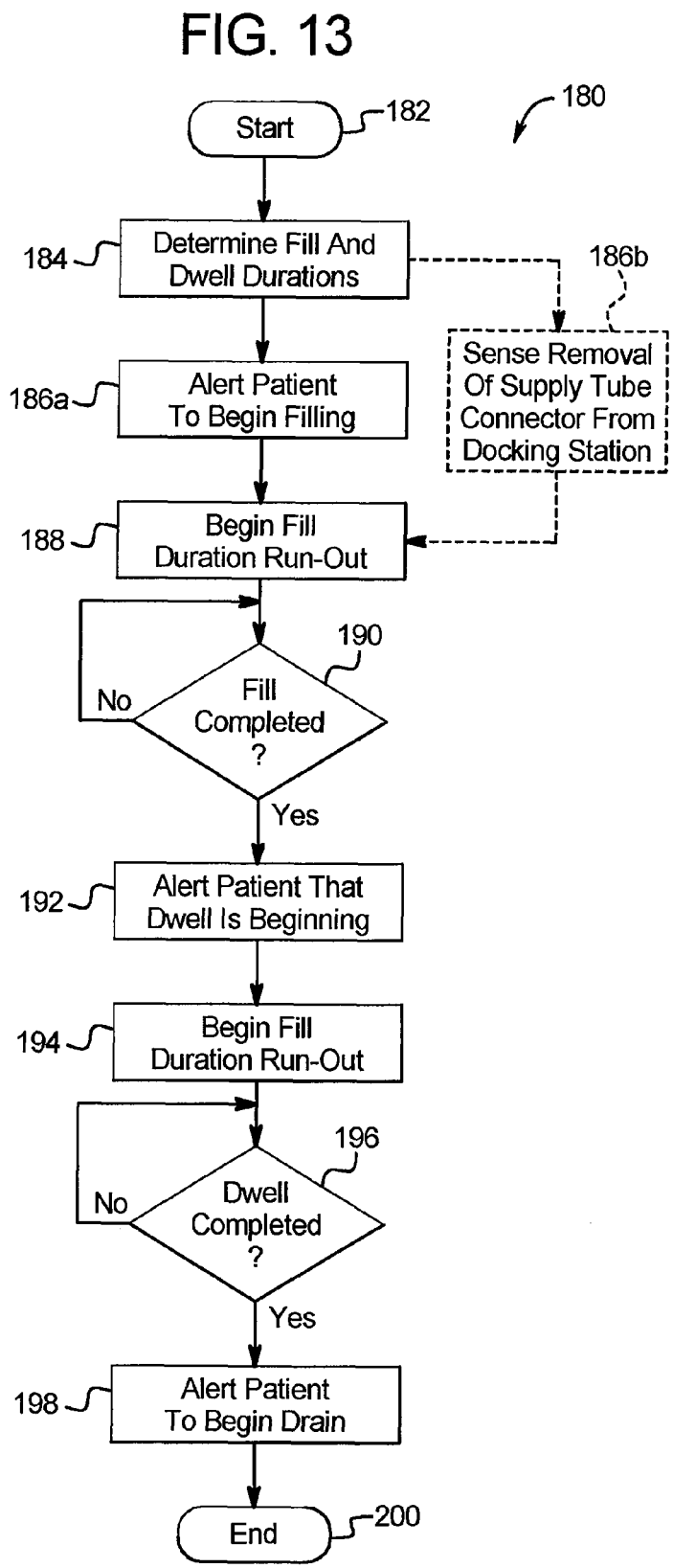

OPTIMIZING THERAPY OUTCOMES FOR PERITONEAL DIALYSIS

PRIORITY CLAIM

This application claims priority as a non-provisional application to, and the benefit of, U.S. Provisional Patent Application for "OPTIMIZING THERAPY OUTCOMES FOR PERITONEAL DIALYSIS", Ser. No. 61/050,114, filed May 2, 2008.

BACKGROUND

The present disclosure relates generally to medical fluid delivery systems and methods. More particularly, this disclosure includes systems, methods and apparatuses for selecting a dwell time for peritoneal dialysis based on an individual patient's response to dialysis, and also based on one or more peritoneal dialysis input parameters. The dwell time is selected to yield the best therapy outcome for that patient based on the dialysis parameters.

Due to various causes, a person's renal system can fail. Renal failure produces several physiological impairments and difficulties. The balance of water, minerals and the excretion of daily metabolic load is no longer possible and toxic end products of nitrogen metabolism (urea, creatinine, uric acid, and others) can accumulate in blood and tissue. Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving.

Hemodialysis and peritoneal dialysis are two types of dialysis therapies used commonly to treat loss of kidney function. A hemodialysis ("HD") treatment utilizes the patient's blood to remove waste, toxins and excess water from the patient. The patient is connected to a hemodialysis machine and the patient's blood is pumped through the machine. Catheters are inserted into the patient's veins and arteries so that blood can flow to and from the hemodialysis machine. The blood passes through a dialyzer of the machine, which removes waste, toxins and excess water from the blood. The cleaned blood is returned to the patient. A large amount of dialysate, for example about 120 liters, is consumed to dialyze the blood during a single hemodialysis therapy. Hemodialysis treatment lasts several hours and is generally performed in a treatment center about three or four times per week.

Another form of kidney failure treatment involving blood is hemofiltration ("HF"), which is an alternative renal replacement therapy that relies on a convective transport of toxins from the patient's blood. This therapy is accomplished by adding substitution or replacement fluid to the extracorporeal circuit during treatment (typically ten to ninety liters of such fluid). That substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is another blood treatment modality that combines convective and diffusive clearances. HDF uses dialysate to flow through a dialyzer, similar to standard hemodialysis, providing diffusive clearance. In addition, substitution solution is provided directly to the extracorporeal circuit, providing convective clearance.

Peritoneal dialysis uses a dialysis solution, also called dialysate, which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

Peritoneal dialysis machines are used to accomplish this task. Such machines are described, for example, in the following U.S. patents, all of which are incorporated by reference in their entirety, as though each patent were set forth herein, page by page, in its entirety: U.S. Pat. Nos. 5,350,357; 5,324,422; 5,421,823; 5,431,626; 5,438,510; 5,474,683; 5,628,908; 5,634,896; 5,938,634; 5,989,423; 7,153,286; and 7,208,092.

There are various types of peritoneal dialysis therapies, including continuous ambulatory peritoneal dialysis ("CAPD"), automated peritoneal dialysis ("APD"), tidal flow APD and continuous flow peritoneal dialysis ("CFPD"). CAPD is a manual dialysis treatment. The patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement. There is room for improvement in the selection of dwell times for each patient.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during APD. A "last fill" occurs at the end of CAPD and APD, which remains in the peritoneal cavity of the patient until the next treatment.

Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, systems clean or regenerate spent dialysate instead of discarding it. These systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroduction of the dialysate into the peritoneal cavity. Additional sensors are employed to monitor the removal of ammonia. CFPD systems are typically more complicated than batch systems.

In each of the kidney failure treatment systems discussed above, it is important to control ultrafiltration, which is the process by which water (with electrolytes) moves across a membrane, such as a dialyzer or peritoneal membrane. For example, ultrafiltration in peritoneal dialysis is a result of transmembrane and osmotic pressure differences between blood and dialysate across the patient's peritoneal membrane. It is also important to control the concentration of metabolic substances in the patient's bloodstream, such as urea concentration, $\beta_2$-microglobulin, creatinine concentration, and so forth. Each of these, along with many other variables, constitutes a peritoneal dialysis outcome.

Each patient is different, possessing for instance, a unique peritoneal membrane, its own separation characteristics, and its unique response to peritoneal dialysis. Each patient is also different with respect to body surface area (BSA) and total body water volume, which also have an effect on transport characteristics. Each patient is different in terms of transport characteristics that relate to the ultrafiltration rate. Each patient is also different in terms of response to dialysis, that is, the amount of water and waste removed in a given time period, using a given fill volume, a particular dialysis fluid, and so forth. What is needed is a way to better control the particular dialysis therapy offered to each patient, so that the treatment will yield the best therapy outcome for that patient, for one or more dialysis input parameters While APD frees the patient from having to manually performing the drain, dwell, and fill steps, a need still exists for CAPD. Some patients prefer the control that CAPD offers. Since the patient is awake during CAPD, the patient can adjust himself/herself during drain to produce more complete drains. Further, many patients who perform APD also perform a midday exchange using a CAPD technique.

Since CAPD does not typically use a machine, advantages of using a machine are not available to the CAPD patient, such as features intended to optimize therapy for the patent. It is therefore desirable to provide a "smart" system that is applicable to both APD and CAPD systems.

SUMMARY

One embodiment is a method for accomplishing peritoneal dialysis. The method includes steps of administering a peritoneal equilibration test (PET) to a patient, determining and recording a patient status as a result of the PET test, and calculating a peritoneal dialysis dwell time based on the patient status and at least one peritoneal dialysis therapy outcome, wherein the dwell time optimizes the at least one peritoneal dialysis therapy outcome for the patient.

Another embodiment is a method for accomplishing peritoneal dialysis. The method includes steps of determining peritoneal transport properties of a patient, determining a classification of the peritoneal transport properties of the patient, and calculating a peritoneal dialysis dwell time based on the classification, a plurality of peritoneal dialysis input parameters, and at least one desired peritoneal dialysis therapy outcome, wherein the dwell time is calculated to maximize the at least one desired peritoneal dialysis therapy outcome.

Another embodiment is a system for calculating a peritoneal dialysis dwell time and conducting peritoneal dialysis. The system includes a processor for operating a peritoneal dialysis machine, a memory of the processor or a memory accessible to the processor, the memory storing a look-up table containing peritoneal dialysis input parameters, peritoneal dialysis therapy outcomes, and peritoneal dialysis dwell times corresponding to the input parameters and dwell times, and a software program stored in the memory of the processor or the memory accessible to the processor for receiving a selection or an input of at least one desired therapy outcome of a patient and calculating a dwell time for the patient for optimizing the at least one peritoneal dialysis therapy outcome for the patient.

Another embodiment is a computer program embodied on a computer readable medium for calculating a peritoneal dialysis dwell time. The computer program includes a code segment for accessing data of a correspondence between a plurality of peritoneal dialysis input parameters, a plurality of peritoneal dialysis therapy outcomes, and a plurality of peritoneal dialysis dwell times. The computer program also includes a code segment that allows a user to input or to select at least one peritoneal dialysis input parameter from the plurality of peritoneal dialysis input parameters and at least one desired therapy outcome; a code segment that receives an indication of the at least one input parameter and at least one desired therapy outcome selected by the user; a code segment that calculates a dwell time corresponding to the at least one desired therapy outcome selected by the user; and a code segment that inputs the dwell time to the dialysis machine.

Another embodiment is a peritoneal dialysis system. The peritoneal dialysis system includes a dialysis cassette and a housing suitable for receiving the cassette, the cassette including at least one pump for pumping dialysis fluid to and from a patient; a microcontroller suitable for operating the peritoneal dialysis system; a memory of the microcontroller or accessible to the microcontroller, the memory including data of a plurality of dialysis input parameters, a plurality of dialysis dwell times, and a plurality of therapy outcomes corresponding to the input parameters and dwell times, wherein a user instructs the microcontroller to select or calculate a dwell time for optimizing at least one dialysis outcome for a patient; and a patient transfer device in communication with the microcontroller.

In yet another embodiment, a system including a smart transfer set is provided. The system includes a docking unit having a docking port that receives and holds the fill or solution bag line, and in one implementation a connector located at an end of the fill line. The connector (or perhaps the fill line itself) bears an identifier that in one embodiment identifies the dialysate solution type, solution volume and solution expiration date.

The docking unit is provided with a reader that reads the identifier. The docking port and the fill line connector are configured to mate, such that the reader can read the identifier. The identifier can be a barcode, in which case the reader is a barcode reader. The identifier is alternatively a radio frequency identifier ("RFID") tag, the reader an RFID reader, in which case the orientation of the connector within the docking port may not be as critical.

The docking unit in one embodiment also includes a computer memory device port, such as a universal serial bus ("USB") port. The port allows the patient to insert a memory device, such as a USB flash drive into the USB port, which allows the patient to download patient specific data to a memory located within the docking unit. That memory can also be used to store information read from the identifier. The docking unit in one embodiment includes processing that processes the information gleaned from the identifier and the patient memory device and develops therapy parameters that are sent from the docking unit to the transfer set. The transfer set is configured to communicate the parameter information to the patient, who uses the information to control a peritoneal dialysis therapy, such as a continuous ambulatory peritoneal dialysis ("CAPD") therapy. To this end, the docking unit is provided with a transmitter (or transceiver) that transmits the parameter information, e.g., wirelessly to a receiver (or transceiver) located within the transfer set.

The transfer set also includes memory and processing, which interface between the receiver and at least one output device for communicating with the patient, such as a light, buzzer or video display. The at least one output device communicates therapy parameter information to the patient, such as when to begin filling from the dialysate supply, when to attempt to have the fill completed, and when to drain spent dialysate, e.g., based on a determined dwell time. While the majority of the processing is done in the docking unit in one embodiment, it is also contemplated to let the transfer set do the majority of the processing, in which case the docking unit serves mainly to transfer information to the transfer set for processing.

The therapy parameter information can be used in a number of ways. In one embodiment, the transfer set also includes an input device that the patient can activate once the patient is done filling from the dialysate container. Here, the docking unit can determine an optimum dwell duration and send it to the transfer set. Once the patient activates the input device, the transfer set beings a running of the optimal dwell duration. The transfer set can include a digital time remaining readout or display that counts down to zero, for example. The transfer set additionally or alternatively includes an alarm or buzzer that communicates when the dwell duration has lapsed, signaling a patient drain.

In another embodiment, the docking unit sends a fill duration and a dwell duration to the smart transfer set. The fill duration is determined principally from the dialysate volume gleaned from the identifier. The dwell duration is determined from the volume, the solution type (e.g., glucose level) and patient parameters, such as PET parameters. The fill duration begins to run, giving the patient an adequate time to fill from the dialysate container. When the patient fill times out, the dwell duration begins to run. The transfer set communicates the running of the dwell duration according to any of the ways discussed above. This embodiment does not require an input device or patient activation.

A third embodiment includes a fill duration and a dwell duration, like the last embodiment. The docking unit also includes a sensor, such as a proximity sensor (capacitive or inductive), which senses the presence or absence of the fill line connector received within the docking port. The proximity sensor is therefore located near the identifier reader. The sensor senses when the connector is removed from the docking unit, at which point it is assumed that the patient is about to connect the connector to the transfer set to begin filling. The sensed removal of the connector is communicated to the transfer set to begin (or begin after a short delay) the running of the fill duration. The running of the fill and dwell durations then proceeds according to the previous embodiment.

It is therefore an advantage of the present disclosure to provide peritoneal dialysis ("PD") systems and methods that optimize therapy dwell times for a patient.

It is another advantage of the present disclosure to provide peritoneal dialysis ("PD") systems and methods that streamline therapy time.

It is a further advantage of the present disclosure to provide peritoneal dialysis ("PD") systems and methods that operate with CAPD as well as APD.

It is still another advantage of the present disclosure to provide peritoneal dialysis ("PD") systems and methods that operate with different types and volumes of dialysate supplies or solutions.

It is still a further advantage of the present disclosure to provide peritoneal dialysis ("PD") systems and methods that preclude the use of an expired solution.

Additional features and advantages are described herein, and will be apparent from the following Detailed Description and the figures.

BRIEF DESCRIPTION OF THE FIGURES

FIG. 11 is a schematic view of one software and electrical layout for the system and method of FIG. 10.

FIG. 12 is a flow chart for one method for implementing a dialysis treatment using a smart patient transfer set.

FIG. 13 is a flow chart for a second method (having two versions) for implementing a dialysis treatment using a smart patient transfer set.

DETAILED DESCRIPTION

Optimizing Therapy

Figure 1:
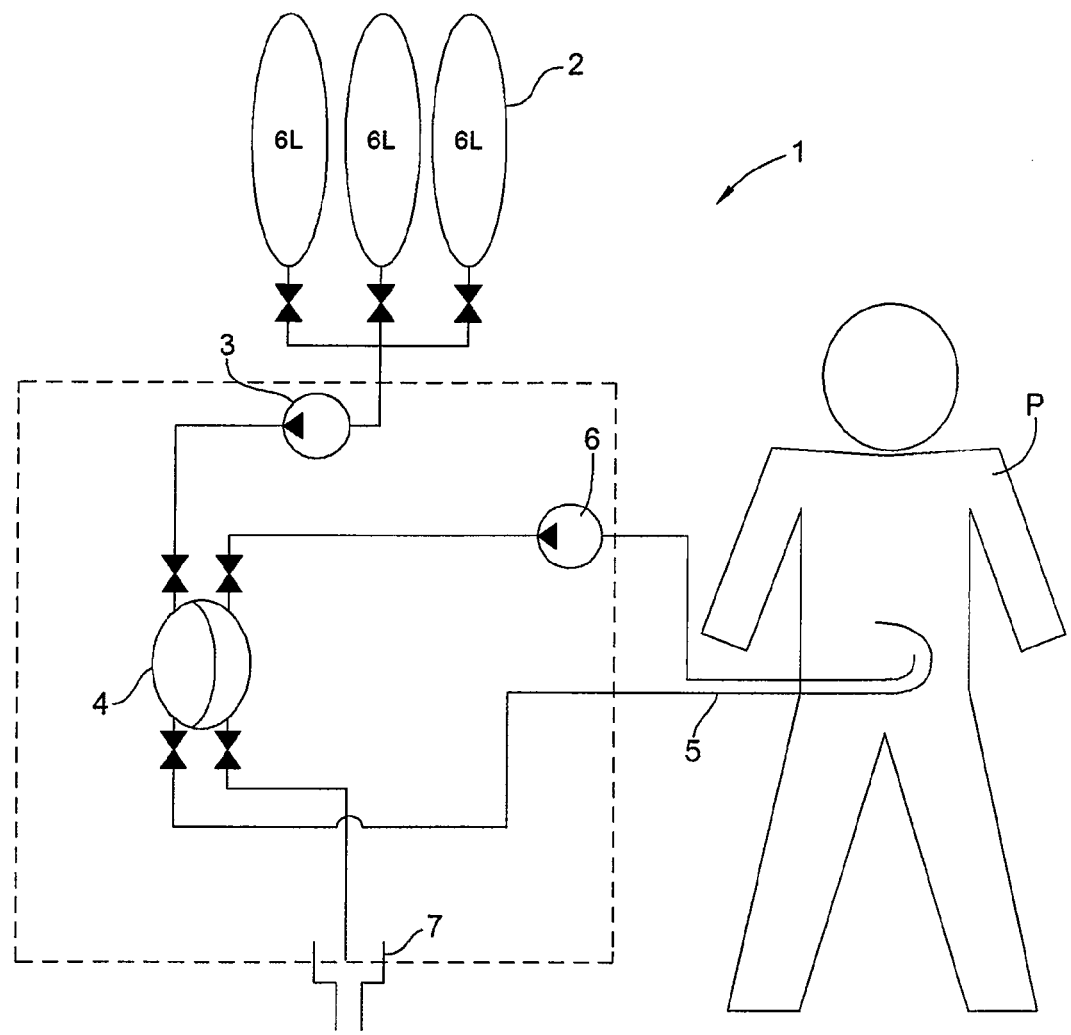
FIG. 1 is a prior art peritoneal dialysis system.

Patients respond differently to peritoneal dialysis. There are a host of variables or parameters involved in peritoneal dialysis. One object of the present disclosure is to discuss these therapy variables or parameters and show how they can be used in tailoring the therapy, and to show how that therapy can be tailored for the best possible outcome for that patient. Optimal execution of peritoneal dialysis therapy can help patients avoid numerous inefficiencies. These inefficiencies include the unnecessary loss of ultrafiltrate due to excessive dwell times, unnecessary carbohydrate absorption from long dwell times, and suboptimal urea ("Kt/V") and creatinine ("Ccr") clearances.

Rather than using a standard 14-15 hour daytime automated peritoneal dialysis ("APD") regimen, or a standard 9-10 nighttime continuous ambulatory peritoneal dialysis ("CAPD") regimen, a dwell time is calculated that is better suited to each patient. The dwell time depends on the patient's transmembrane transport capabilities, usually expressed as the patient's status as determined by a peritoneal equilibration test ("PET"). As an example of one benefit, carbohydrate ("CHO") absorption does not peak during peritoneal dialysis dwell times, but continues at a steady pace. The carbohydrate (e.g., glucose or icodextrin) in peritoneal dialysis solutions creates an osmotic gradient, enabling mass transport through the peritoneum. It is well known that this osmotic gradient decreases drastically during a long dwell time, most likely caused by absorption of the CHO itself into the peritoneum. Accordingly, shorter dwell times will reduce CHO absorption and free the patient for other activities.

One basic difference among patients is the rate at which water and metabolic wastes pass from the patient's bloodstream through the peritoneal membrane. Once the water and wastes pass through the peritoneal membrane, they are absorbed into the dialysis therapy fluid that has been placed into the patient's peritoneal cavity, and then removed from the patient. A peritoneal equilibration test (PET) determines the relative rate of transmembrane transport. Patients can then be classed as high-rate transporters, high-average transporters, low-average transporters, or low-rate transporters, depending on the speed of waste removal. Other classification schemes may also be used, such as simply high, average, and low transporters. Patients may also be classified in terms of their total body surface area (BSA), e.g., a high, average, or low BSA. The total body water volume may also be used as an input parameter to help predict transport characteristics of the patient.

In general, the rate of water removal is different from the rate of waste removal, and both depend on the patient transporter type. For example, fast transporters can quickly pass metabolic waste, but glucose from the dialysis solution is rapidly absorbed into the body. As a result, glucose concentration in the dialysate decreases and the osmotic gradient diminishes within a relatively short period of time, depending on the patient transporter type. For instance, high transporters may benefit more from short dwell times, such as those used in automated peritoneal dialysis (APD), where the effect of high osmotic gradients is still present.

Conversely, the osmotic gradient will be sustained for a longer period of time in the case of a low transporter patient, resulting in a larger volume of ultrafiltrate removal. Such a patient will likely benefit from a longer dwell time, such a continuous ambulatory peritoneal dialysis (CAPD) and with perhaps only a single nighttime exchange. Much useful information about a patient's response to therapy can be learned from administering the PET test to the patient. The results of the PET test can then be used to administer the therapy that would lead to the best outcome for that patient.

Another variable in peritoneal dialysis is the fill volume, that is, the volume infused into the patient's peritoneum at the beginning of the dwell. The fill volume should be tailored to the comfort of the patient and the efficacy of the therapy. Fill volumes typically range from about 1.5 liters to about 3 liters, i.e., from about 1500 ml to about 3000 ml.

Therapy outcomes differ based on the fill volume, and they also differ based on the particular therapy fluid or peritoneal dialysis fluid used. For example, peritoneal dialysis fluids, such as Dianeal® from Baxter International, Deerfield, Ill., U.S.A., may contain from 1.5% to 4.25% glucose. Other solutions may also be used. The glucose is used to provide a large osmotic pressure gradient between the infused dialysate solution and the patient's bloodstream, in order to draw excess water from the patient, i.e., ultrafiltrate. Other fluids may have other osmotic agents, such as icodextrin, e.g., 7.5% icodextrin in Extraneal® from Baxter International, which is typically used for longer dwell times.

The inputs to a particular dialysis therapy are thus seen to include at least the patient characteristics, i.e., his or her unique response to therapy, the therapy solution used, the total volume of therapy solution, and the dwell time used for the therapy. As discussed above, the outputs of the therapy are the results of the therapy. These results include the amount of water removed, typically expressed as net ultrafiltrate volume.

Other results or therapy outcomes include urea clearance, sometimes expressed as Kt/V, creatinine clearance (Ccr), and total carbohydrate absorption (CHO, also known as glucose or icodextrin absorption). Other therapy outcomes may also be measured, such as sodium removal, phosphate clearance, and middle molecule clearances, e.g., $\beta_2$-microglobulin. Note that an optimum therapy outcome requires high removal of urea and creatinine, as well as other wastes and ultrafiltrate. However, carbohydrate absorption should be minimized. As noted above, water can be transported both ways across the peritoneal membrane. Thus, net ultrafiltrate should be positive, with water removed, rather than having water absorbed from the peritoneal dialysis fluid, which would constitute negative ultrafiltration, and which is possible in a high transporter with a long dwell time.

In order to optimize therapy outcomes for individual patients, kinetic modeling has been undertaken using the above variables. Kinetic modeling software, PD Adequest 2.0™, is from Baxter International, Deerfield, Ill., U.S.A. This program uses a three-pore model of a patient's peritoneal membrane, and accepts choices of high, high-average, low-average, and low patient parameters, and uses a body surface area (BSA) input from 1.7 to 2.0 m². In developing the data presented herein, fill volume inputs of 1.5 L, 2 L, 2.5 L and 3 L were used, as were therapy fluid inputs of 1.5%, 2.5% and 4.25% glucose Dianeal, and Extraneal with 7.5% icodextrin.

The results were tabulated in tables and plotted on graphs. An example of different dwell times and the modeled results is depicted in Table 1 below.

TABLE 1

| high transporter, 2 L fill, 2.5% Dianeal ® | | | | | |
|---|---|---|---|---|---|
| Dwell time, hours | UF, ml | Urea removal, g | Creatinine removal, L/wk/1.73 | Glucose absorption, g. | Urea clearance, Kt/V |
| 2.5 | 133 | 1.84 | 10.7 | 30.5 | 0.32 |
| 5 | 69 | 2.01 | 12.6 | 38.6 | 0.35 |
| 6 | 24 | 1.99 | 12.7 | 40.1 | 0.34 |
| 10 | −184 | 1.81 | 11.87 | 42.6 | 0.31 |

Table 1 clearly shows that a shorter dwell time is better for a high-transporter patient. After 2.5 hours, the net ultrafiltrate (UF) is highest, 133 ml net ultrafiltrate, with high levels of urea and creatinine removal as shown. Allowing the therapy fluid to dwell for five hours has a deleterious effect: the net ultrafiltrate has decreased by about half, to abut 69 ml, and glucose absorption has increased by about 25% to 38.6 g. Because the volume of ultrafiltrate continues to decrease, this patient may already have reached a point of diminishing returns, at least for ultrafiltrate volume.

The only benefit from increased dwell time is a small increase in urea and creatinine removal. However, if there were some medical reason to do so, one could select the urea removal or creatinine removal as the outcome of interest, and select the appropriate dwell time, 5 hours for urea removal or 6 hours for creatinine removal. This selection would optimize the value of the particular desired outcome, whether net ultrafiltrate, urea removal, or creatinine removal, or the removal of other solutes, such as phosphate or $\beta_2$-microglobulin that are not quantified here.

Another example for a high-transporter patient is depicted in Table 2 below, in which the principal change is to use 2.5 L fill volume rather than 2 L.

TABLE 2 high transporter, 2.5 L fill, 2.5% Dianeal ®

| Dwell time, hours | UF, ml | Urea removal, g | Creatinine removal, L/wk/1.73 | Glucose absorption, g. | Urea clearance, Kt/V |
|---|---|---|---|---|---|
| 3 | 165 | 2.30 | 13.32 | 38.0 | 0.40 |
| 6 | 86 | 2.52 | 15.78 | 48.4 | 0.44 |
| 7 | 40 | 2.50 | 15.91 | 50.0 | 0.43 |

Table 2 depicts results of using additional fill volume and slightly longer dwell times. Using the additional 500 ml of fill volume has caused an increase in net ultrafiltrate, to 165 ml, with increases in urea and creatinine removal over the amounts removed with 2.5 hours dwell and a 2 L fill volume. While these are desirable, there has been an increase in glucose absorption. The caregiver or medical professional can decide whether the increased ultrafiltration, urea removal and creatinine removal is sufficient to justify an increase in glucose absorption. The desired outcome is then used to select the dwell time for the patient, as well as whether it is desirable to use 2 L fill volume or 2.5 L fill volume. Other examples are given below for other transporter conditions.

TABLE 3 high-average transporter, 2 L fill, 2.5% Dianeal ®

| Dwell time, hours | UF, ml | Urea removal, g | Creatinine removal, L/wk/1.73 | Glucose absorption, g. | Urea clearance, Kt/V |
|---|---|---|---|---|---|
| 3.5 | 181 | 2.21 | 10.04 | 30.04 | 0.33 |
| 6 | 125 | 2.35 | 11.87 | 36.93 | 0.35 |
| 8 | 40 | 2.30 | 12.26 | 39.82 | 0.34 |

TABLE 4 high-average transporter, 2.5 L fill, 2.5% Dianeal ®

| Dwell time, hours | UF, ml | Urea removal, g | Creatinine removal, L/wk/1.73 | Glucose absorption, g. | Urea clearance, Kt/V |
|---|---|---|---|---|---|
| 4 | 222 | 2.74 | 12.29 | 36.77 | 0.41 |
| 7 | 160 | 2.94 | 14.82 | 46.00 | 0.44 |
| 10 | 29 | 2.86 | 15.41 | 50.41 | 0.43 |

Tables 3 and 4, for high-average transporters, demonstrate a shift of peak time points to longer dwell times. The ultrafiltration volumes are higher at these longer dwell times, higher than the ultrafiltration volumes for the high-transporter Tables 1 and 2. There are also greater urea and creatinine removals.

TABLE 5 low-average transporter, 2 L fill, 2.5% Dianeal ®

| Dwell time, hours | UF, ml | Urea removal, g | Creatinine removal, L/wk/1.73 | Glucose absorption, g. | Urea clearance, Kt/V |
|---|---|---|---|---|---|
| 4 | 209 | 2.45 | 9.14 | 26.80 | 0.32 |
| 7 | 173 | 2.67 | 11.34 | 34.50 | 0.35 |
| 11 | 28 | 2.58 | 12.08 | 39.64 | 0.33 |

TABLE 6 low-average transporter, 2.5 L fill, 2.5% Dianeal ®

| Dwell time, hours | UF, ml | Urea removal, g | Creatinine removal, L/wk/1.73 | Glucose absorption, g. | Urea clearance, Kt/V |
|---|---|---|---|---|---|
| 5 | 258 | 3.10 | 11.69 | 34.37 | 0.40 |
| 9 | 193 | 3.35 | 14.50 | 44.57 | 0.43 |
| 13 | 41 | 3.23 | 15.17 | 49.64 | 0.42 |

Tables 5 and 6 demonstrate shift of peak time points to even longer dwell times for low-average transporter patients. The ultrafiltration volumes are higher at these longer dwell times, higher than the ultrafiltration volumes for the high-transporter Tables 1 and 2 and for high-average transporter Tables 3 and 4, especially with a 2.5 L fill. There are also greater urea and creatinine removals, urea removal peaking at about 9 hours.

TABLE 7 low transporter, 2 L fill, 2.5% Dianeal ®

| Dwell time, hours | UF, ml | Urea removal, g | Creatinine removal, L/wk/1.73 | Glucose absorption, g. | Urea clearance, Kt/V |
|---|---|---|---|---|---|
| 6 | 335 | 2.24 | 9.01 | 26.94 | 0.37 |
| 9 | 287 | 2.33 | 10.66 | 32.83 | 0.38 |
| 15 | 49 | 2.16 | 11.63 | 39.42 | 0.35 |

TABLE 8 low transporter, 2.5 L fill, 2.5% Dianeal ®

| Dwell time, hours | UF, ml | Urea removal, g | Creatinine removal, L/wk/1.73 | Glucose absorption, g. | Urea clearance, Kt/V |
|---|---|---|---|---|---|
| 7 | 409 | 2.79 | 11.14 | 33.42 | 0.46 |
| 11 | 342 | 2.91 | 13.48 | 41.76 | 0.48 |
| 16 | 148 | 2.78 | 14.58 | 47.97 | 0.45 |

Tables 7 and 8 show that the low transporter patients benefit from longer dwell times, in clear contrast with the high transporter patients. The ultrafiltration volumes are significantly increased, and may already have peaked since the volumes are decreasing. Urea removal peaks at 9 and 11 hours respectively These data can be used to select a dwell time for the best possible outcome of a dialysis therapy session for a specific patient. Dialysis therapy is typically conducted with a peritoneal dialysis machine, such as the machine depicted in FIG. 1. One suitable peritoneal dialysis machine is the HomeChoice® peritoneal dialysis machine from Baxter International, Deerfield, Ill., U.S.A. A patient P is connected to a dialysis machine 1, shown within the dashed lines, with a patient access device 5, such as an implanted catheter as shown. The catheter may be a single lumen or double lumen catheter, or another type of access device may be used. A plurality of containers 2 of dialysis solution is connected to the dialysis machine, as shown, through valves or other connectors. A pump 3 is used to transport dialysis fluid from the containers 2, one at a time, through a balance chamber 4 to the peritoneal cavity of the patient P through the access device. After the peritoneal dialysis solution has remained within the patient for the desired dwell time, the same pump 3 or another pump 6 may be used to pump the spent dialysis solution through the balance chamber 4 and then to a drain 7.

Figure 2:
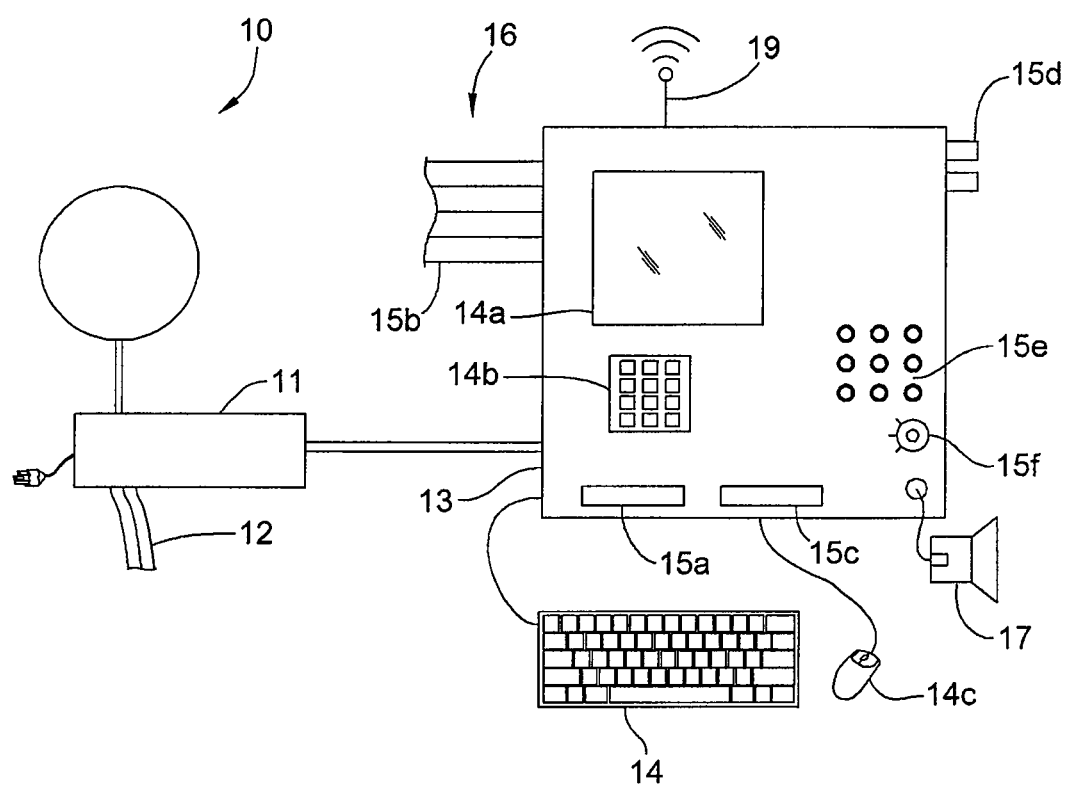
FIG. 2 is a control system for a peritoneal dialysis system according to the present disclosure.

In embodiments discussed herein, a dialysis machine 1 may be used with a dialysis control system 10 as depicted in FIG. 2. Dialysis control system 10 includes an operating portion, such as the peritoneal dialysis machine depicted in FIG. 1, including fluid lines 12 for connection to patient access device 15. The operating section 11 performs dialysis for the patient under the supervision of a control unit 13. Control unit 13 in one embodiment has at least an input keypad 14, control panel 14*a*, which may be a touch screen, input number pad 14*b*, and mouse 14*c*. The control unit will also include input drive 15*a*, which may be suitable for a floppy drive or for a CD drive. The computer in this embodiment is configured with a port for Internet access 15*b*, as well as additional inputs and outputs, including ports 16. The additional input ports may be any combination of serial ports, such as USB ports, or parallel ports.

In some embodiments, the control unit will be adapted to receive commands from a remote control unit, and will include an IR receiver 15*c* for a hand-held remote. Inputs/outputs may include an optical input or output 15*d* and other digital or analog inputs. Control portion 15*e* includes a series of controls knobs or switches for operating the dialysis machine. A speaker output 17 can alert the patient or a caregiver if there is an emergency or other malfunction of the dialysis machine. There is also a visual alarm 15*f* for alerting the patient or caregiver. The control section includes an antenna 19 for receiving remote commands or information. The antenna may be used for communication with a wireless device for the patient, as discussed below. The antenna may also be used for wireless (WiFi) internet access or may be used for remote, but closer, commands.

Figure 3:
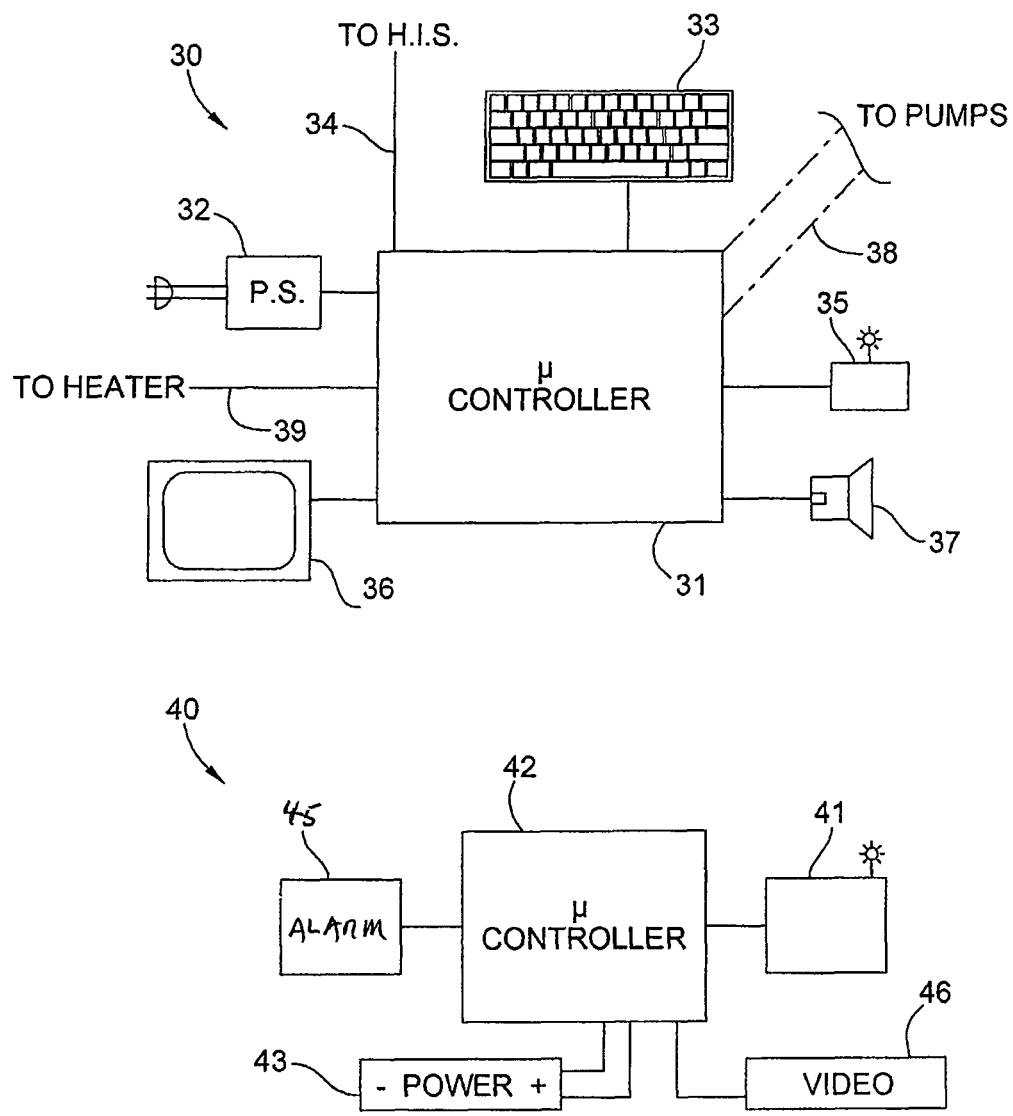
FIG. 3 is schematic view of a more detailed control system for a peritoneal dialysis system.

FIG. 3 depicts a closer view of the control portions 30 of the dialysis machine 10. Machine control portion 30 is in communication with a "smart" patient control portion 40. As seen in FIG. 3, the communication is wireless, for convenience and mobility of patients, such as mobile CAPD patients. However, those with skill in the art will recognize that a wire harness or cable could also connect the two portions. Dialysis machine control portion 30 includes a supervisory microcontroller 31, which receives power from a power supply 32. The microcontroller receives inputs from at least a keypad 33, and may also receive data and commands from a wired connection 34, such as from a clinic or hospital information system. Inputs may also be received from the patient via wireless connection and radio 35. The microcontroller has outputs to a video monitor 36, a speaker 37, as well as controls to the dialysate pumps 38 and a heater 39 for the dialysate. The machine control system includes at least one memory as a part of the microcontroller 31 or accessible by the microcontroller 31.

The patient control portion 40, as noted above, is not attached to the dialysis machine, enabling a mobile patient to move about without a wire harness or other connecting cable. Of course, other embodiments may include a cable, infrared (IR) or RF communications instead of the radio described herein. The patient control portion includes a separate microcontroller 42 and power supply 43, such as a battery 42. The controller 42 receives input from the radio 41, with outputs through the radio and to an audio alarm or speaker 45 and a small video monitor 46. In some embodiments, the patient control portion may also include switches or other electromechanical inputs for signaling the microcontroller 42 or for controlling the operation of the patient control portion 40.

The signal processing circuitry and radio 41 or wireless receiver/transmitter are small and compact, and are easily placed on the patient at the access site, such as in a "smart" module or connector. One radio that works is a wireless module in accord with ZigBee/IEEE 805.15.4. This is a standard for a very low power radio system with a very limited range, about 10-20 feet. Modules made in accordance with this standard may be purchased from Maxstream, Inc., Lindon, Utah, U.S.A., Helicomm, Inc., Carlsbad, Calif., U.S.A., and ANT, Cochrane, Alberta, Canada. The module is very small, and may be about 2 cm square (about 1 inch square), and about 3 mm thick (⅛ inch). The patient control portion 40, as noted, is intended for close proximity, within range of the ZigBee module, of about 10-20 feet, of the dialysis machine. Thus, the local portion or signal module is conveniently small and unobtrusive for the patient, but fully capable of communication and control with the machine control portion 30.

Figure 4A:
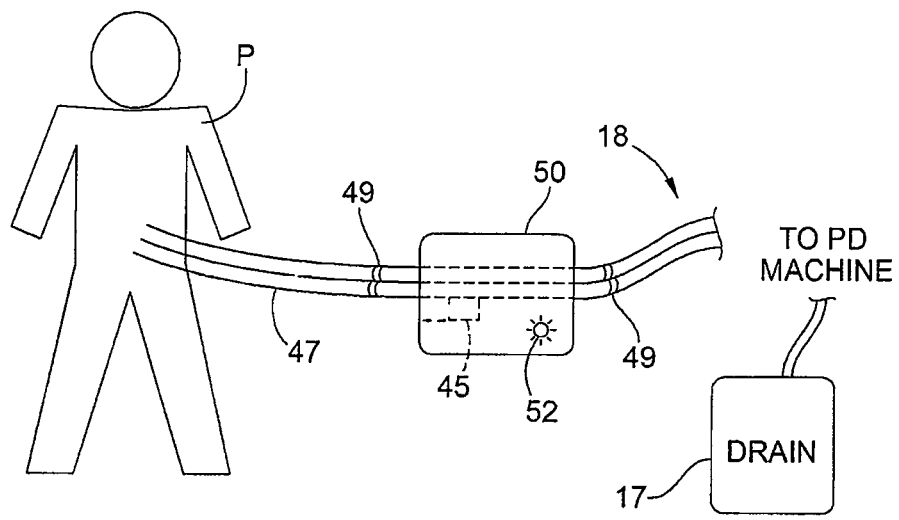
FIGS. 4A and 4B are two embodiments of remote connectors that may be used with the control system.

The patient may use the patient control portion or may simply use the dialysis machine, such as the embodiment depicted in FIG. 2. In one embodiment, shown in FIG. 4*a*, the patient P is connected to the dialysis machine through patient line 18, through patient control device and transfer set 50, and a catheter serving as a peritoneal access device 47. Patient control device 50 is connected via luer connectors 49, or other suitable connectors. The present day transfer set, into which the patient control device can be integrated, includes a length of tubing with a clamp, the length of tubing including one luer connector, such as a titanium luer, for connecting to the patient access device and a second luer for connecting to the patient line. Those who have skill in the art will recognize that patient transfer sets vary in regards to the connectors used, and also vary in the clamp (not shown) or clamps used.

In this embodiment, the patient access device 47 is a double-lumen catheter and the patient line 18 includes two lengths of tubing. Patient control device 50 includes an audio alarm or speaker 45 and a lamp 52, such as an LED, to alert a patient when the therapy session has begun or has ended. Two lamps may be used, such as a green lamp when therapy has begun and a red lamp to alert the patient that the therapy session has ended. In one embodiment, patient control device 50 can be disengaged and separated from the tubing or transfer set for cleaning, replacement, and so forth. In another embodiment, the device cannot be disengaged and is embedded within the transfer set in such a manner as to extend the functions of the transfer set, without significantly impacting the volume or area (footprint) of the transfer set.

Figure 4B:
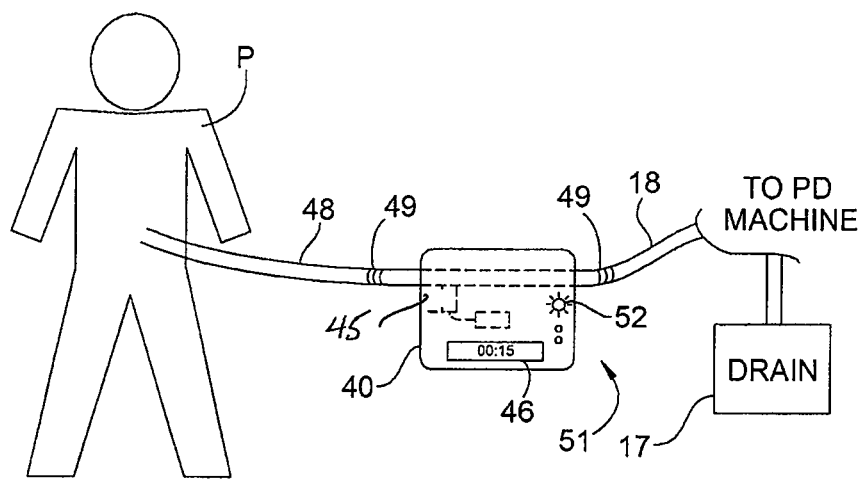

Another embodiment 40 of the patient control device, and its application, is depicted in FIG. 4B. Patient P is connected to the dialysis machine through a single-lumen patient line 18, patient control device and transfer set 40, and a single-lumen catheter 48 serving as a patient access device. Patient control device 40 is connected via luer connectors 49 or other suitable connectors. The patient control device 40 includes a small video output 46 and a lamp 52. An audio alarm 45 may be used to signal the patient to begin or end a therapy session. The video output 46 is suitable for displaying a time remaining on the dialysis session. Lamp 52 may be used to signal the patient, as discussed above. The patient control device 40 also includes two switches 51, suitable for allowing the patient to respond to queries from the microcontroller 42. The switches, in this embodiment, are "yes" and "no" switches that are suitable for responding to queries from the controller, such as "shall we start the dialysis session?" or "please enter a start time for the dialysis session."

Figure 5:
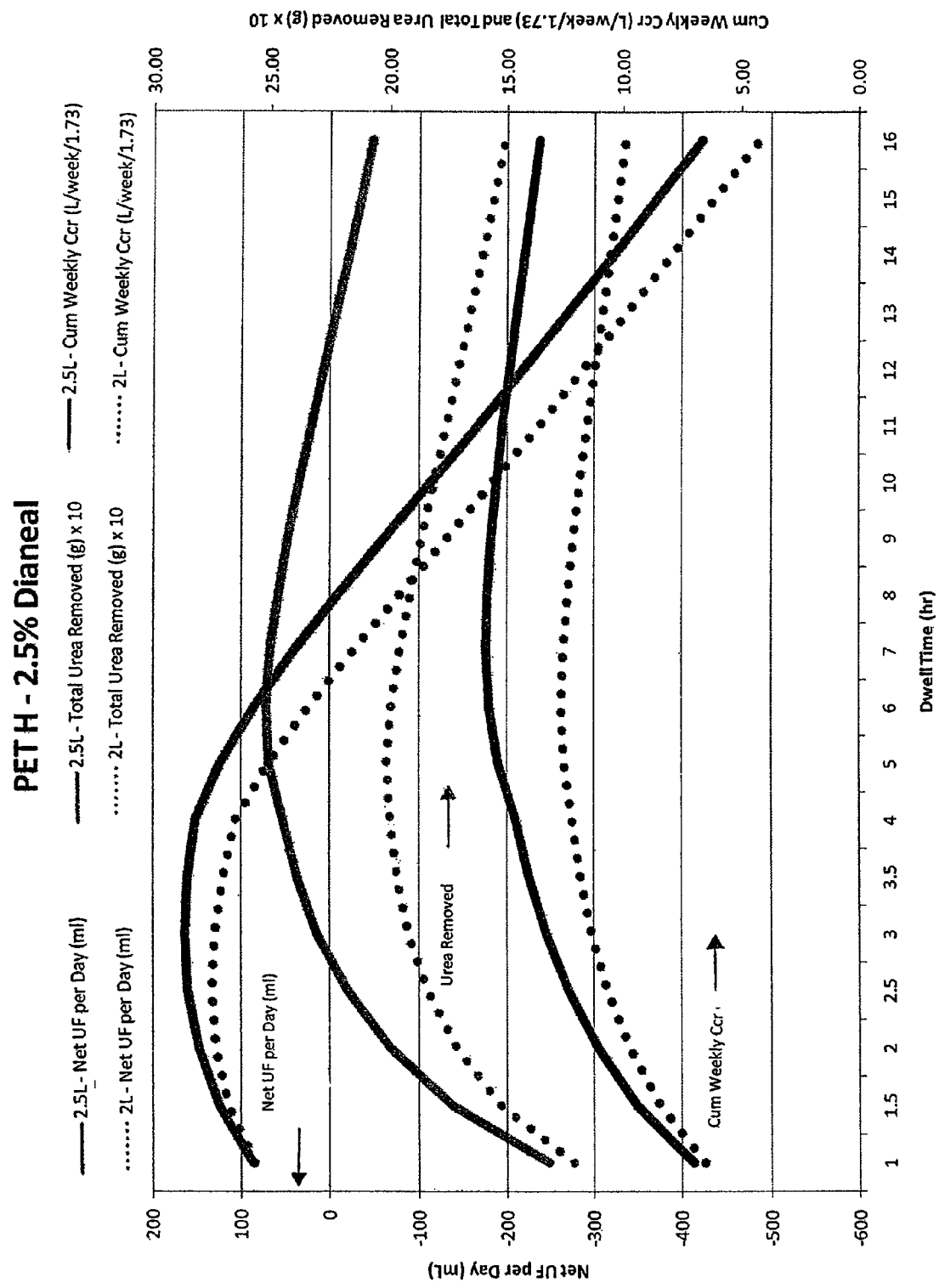
FIGS. 5 to 8 are graphs of peritoneal parameters and values of peritoneal parameters as they relate to dwell times for the peritoneal dialysis fluid.

In addition to tabular data, as might be expected in a look-up table, the correspondence between dwell times and therapy outcomes can be expressed as equations, and can be presented in graphical format, as shown in FIGS. 5-8. Each of these figures depicts performance for a patient according to the PET test status of the patient, as explained above for the tables. FIG. 5, for instance, for a high-transporter patient (H), depicts therapy outcomes for patients that have been dialyzed with 2 L or 2.5 L of 2.5% glucose Dianeal® peritoneal dialysis solution. The solid lines depict 2.5 L results and the dotted lines depict 2 L results, for net ultrafiltrate (read on the scale on the left side of the graph), urea removed (read on the scale on the right side of the graph), and creatinine removal (also read on the scale on the right side of the graph). The data demonstrate that net ultrafiltrate peaks at about 2.5 or 3 hours for both a 2 L or a 2.5 L fill for a high-transporter patient. Urea removal peaks at about 4 hours with a 2 L fill (dotted line), or at about 6 hours for a 2.5 L fill (solid line). For creatinine, clearance peaks at about 6 hours for a 2 L fill and at about 7 hours for a 2.5 L fill.

Using this data, a patient or a caregiver, such as a medical professional, can select a dwell time based on the desired outcome, e.g., 3 hours dwell time with a 2.5 L fill for maximum ultrafiltrate. If the desire is to accommodate more than one desired outcome, a compromise can be reached by interpolating between the desired outcomes. For instance, both high ultrafiltrate and high urea removal may be desired. For a 2.5 L fill, maximum urea removal occurs at about 6.5 hours. A dwell time between 3 and 6.5 hours may be selected, based on averaging the two times, such as 3+6.5=9.5, and then dividing by two, to arrive at about 4.75 hours. If one outcome or therapy result is deemed more important, a weighted average may be used. For example, if ultrafiltration is more important, the time for the best ultrafiltration outcome may be multiplied by a weighting factor of 2, while using a weighting factor of 1 for the creatinine dwell time. In this case, the result would be (3×2)+6.5=12.5, and then dividing the result by three, to arrive at a dwell time of about 4.2 hours. Weighting factors may be pre-selected and may be programmed into a computer program to calculate a resultant dwell time.

Figure 6:
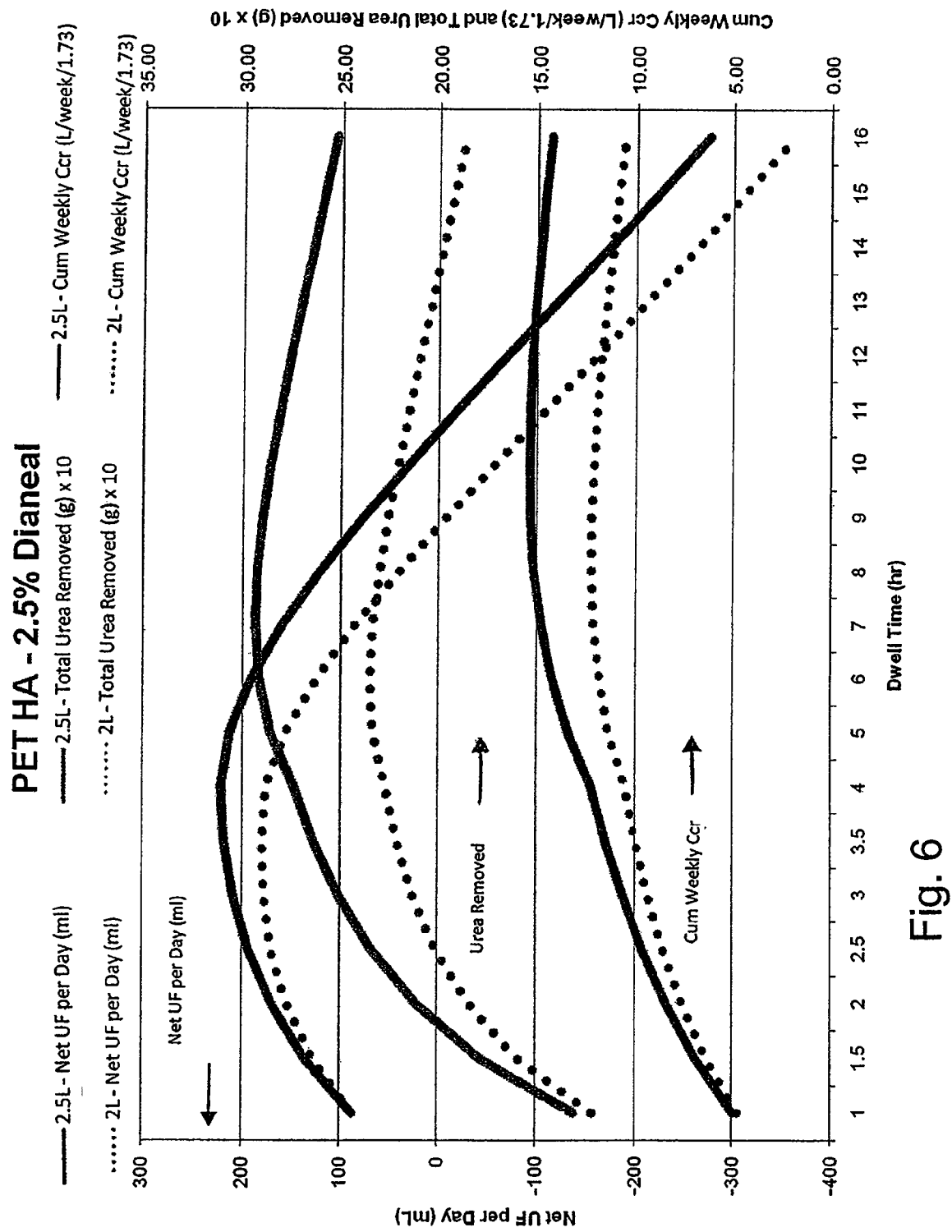

FIG. 6 depicts therapy outcomes for a patient whose PET status is that of a high-average (HA) transporter. The kinetic modeling was accomplished using parameters of 2.5% glucose Dianeal®, with 2 L and 2.5 L fill volumes. In these results, the creatinine has a very subtle peak removal at about 9 hours, with very little effect from adding or subtracting two hours from the dwell time. The ultrafiltration and urea removal curves are shifted somewhat to the right, with greater dwell times, in comparison with those of FIG. 5 for H transporters. In other words, HA transporters act more slowly and need more time than H transporters, which is to be expected.

Figure 7:
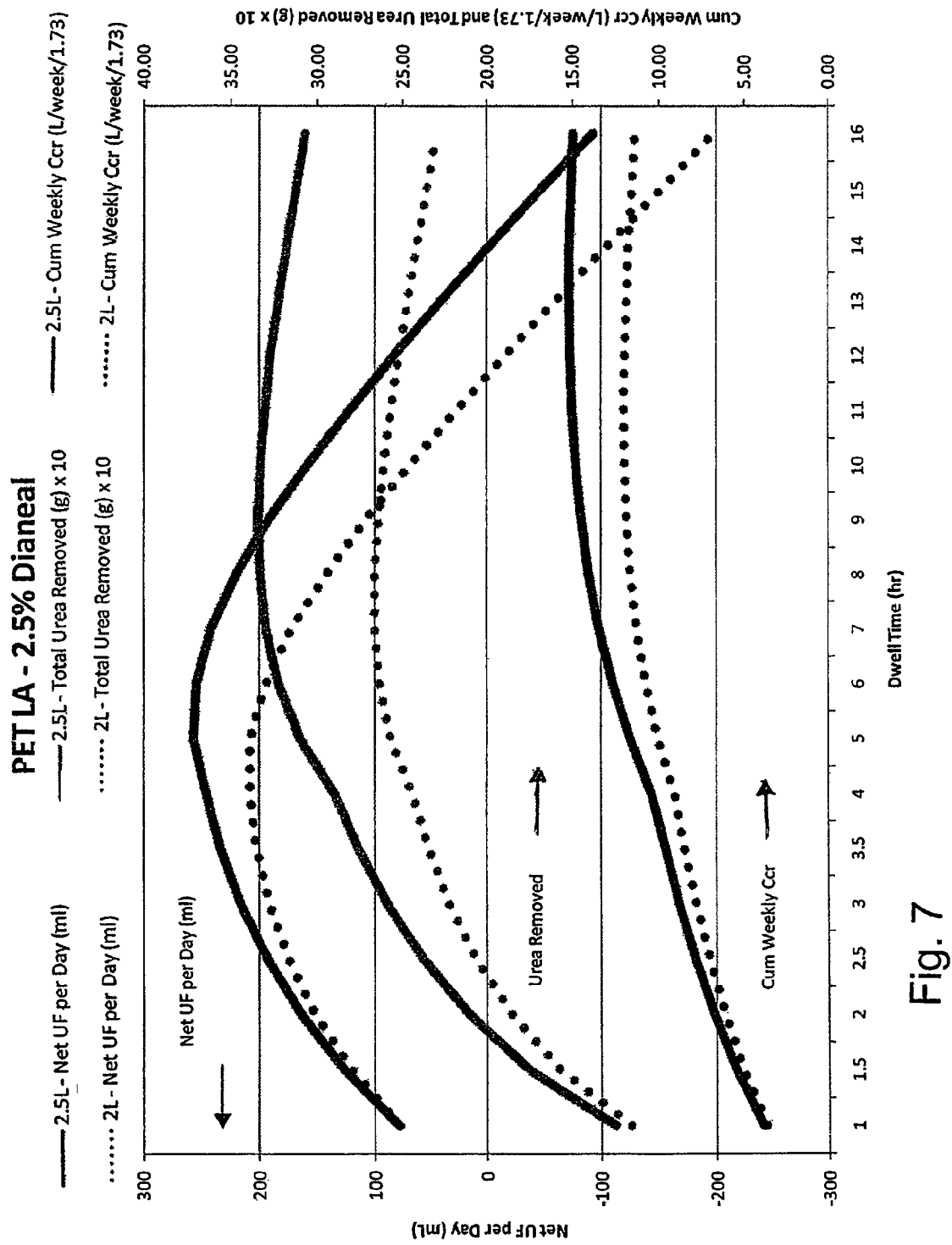

FIG. 7 depicts results for low-average (LA) transporters, with the same input parameters of 2.5% glucose Dianeal®, with 2 L and 2.5 L fill volumes. The curves for creatinine now have no peak, suggesting that longer dwell times result in additional cumulative creatinine transport. The curves for urea removal now have more subtle peaks, and the curves for both urea and ultrafiltrate are shifted toward even longer dwell times.

Figure 8:
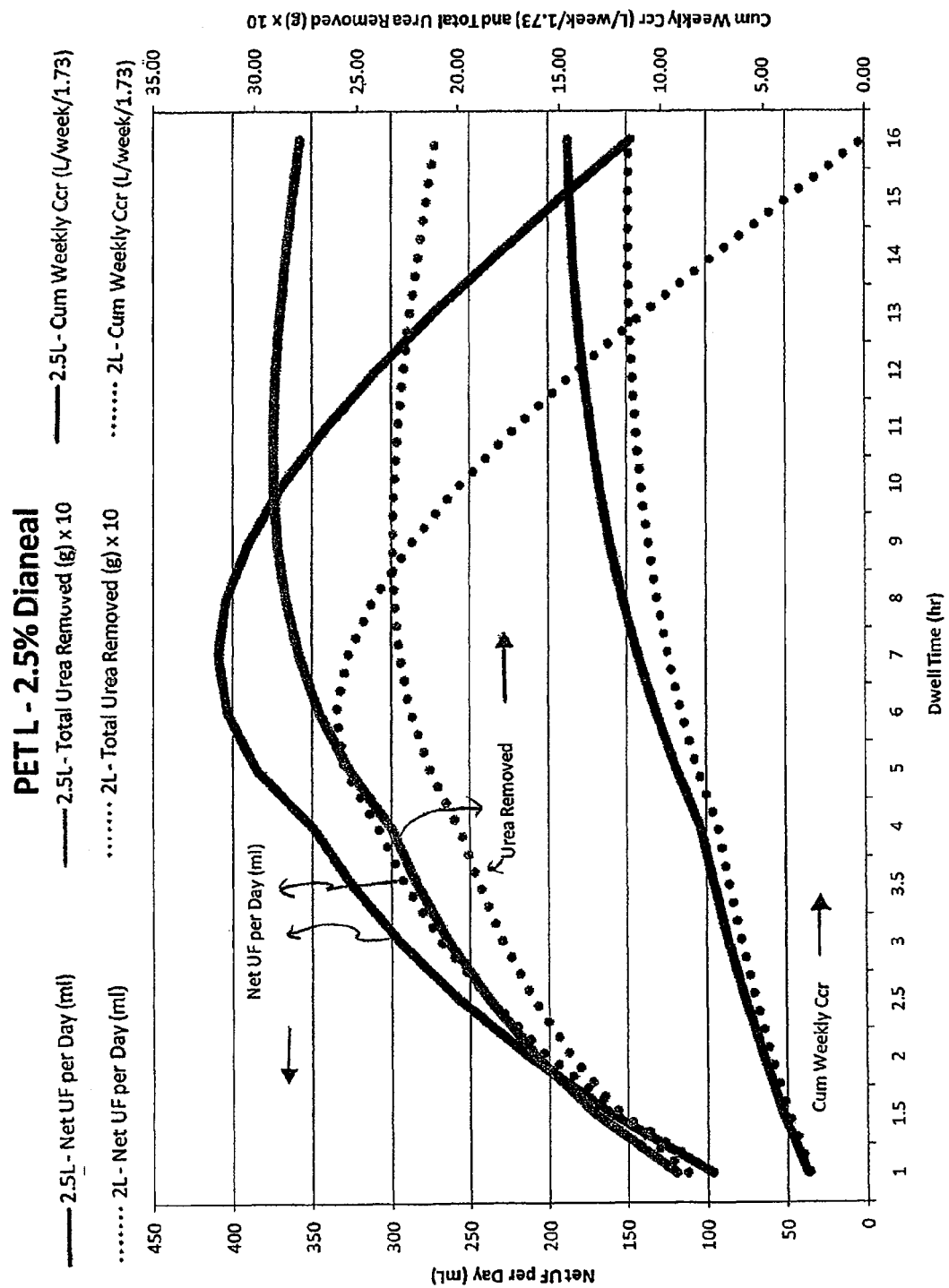

FIG. 8 demonstrates great differences in transport properties for low (L) transporter patients. In comparison with patients having higher transport status, low transporters have much higher rates of ultrafiltration and slower rates of waste removal. The ultrafiltration curves, the highest two curves on the left side of the chart, have much higher rates (note that the left-hand scale is changed from the previous graphs). After about 6-7 hours, depending on the fill, the ultrafiltration reverses, i.e., dialysis solution is being absorbed into the patient's peritoneum, rather than ultrafiltrate being expressed into the dialysis solution. The ultrafiltration curves are thus the lowest two curves at the longest dwell times (right side of chart). Creatinine removal does not peak, even at 16 hours, while urea removal peaks at about 9 hours (2 L fill) and about 10 hours (2.5 L fill).

Many additional data may also be used to understand the transport behavior of peritoneal dialysis patients, as shown in the tables below, which concern respectively, performance at fill volumes of 1500 ml (1.5 L), 2000 ml (2 L), 2500 ml (2.5 L), and 3000 ml (3 L). These data are depicted respectively in Tables 9-12.

TABLE 9

1500 ml (1.5 L) volume fill

| | 1.5% Dianeal Solution | | | 2.5% Dianeal solution | | | 4.25% Dianeal Solution | | | Extraneal Solution | | |
|---|---|---|---|---|---|---|---|---|---|---|---|---|
| | Dwell | Net UF | Kt/V | Dwell | Net UF | Kt/V | Dwell | Net UF | Kt/V | Dwell | Net UF | Kt/V |
| H | 3.0 | 18 | | 2.0 | 103 | | 3.0 | 294 | | 16 | 534 | |
| | 3.5 | | .24 | 4.0 | | .26 | 5.0 | | .29 | 16 | | .35 |
| HA | 1.5 | 25 | | 2.5 | 140 | | 4.0 | 394 | | 16 | 594 | |
| | 4.0 | | .24 | 5.0 | | .28 | 6.0 | | .31 | 16 | | .35 |
| LA | 2.0 | 28 | | 3.5 | 164 | | 5.0 | 463 | | 16 | 548 | |
| | 5.0 | | .29 | 6.0 | | .26 | 7.0 | | .31 | 16 | | .34 |
| L | 2.5 | 5.6 | | 5.0 | 260 | | 7.0 | 693 | | 16 | 665 | |
| | 6.0 | | .25 | 7.0 | | .29 | 9.0 | | .36 | 16 | | .37 |

TABLE 10

2000 ml (2 L) volume fill

| | 1.5% Dianeal Solution | | | 2.5% Dianeal solution | | | 4.25% Dianeal Solution | | | Extraneal Solution | | |
|---|---|---|---|---|---|---|---|---|---|---|---|---|
| | Dwell | Net UF | Kt/V | Dwell | Net UF | Kt/V | Dwell | Net UF | Kt/V | Dwell | Net UF | Kt/V |
| H | 1.5 | 24 | | 2.5 | 133 | | 3.5 | 375 | | 16 | 651 | |
| | 4.0 | | .32 | 5.0 | | .35 | 6.0 | | .38 | 16 | | .46 |
| HA | 2.0 | 34 | | 3.5 | 181 | | 5.0 | 500 | | 16 | 700 | |
| | 5.0 | | .32 | 8.0 | | .35 | 7.0 | | .41 | 16 | | .46 |

TABLE 10-continued 2000 ml (2 L) volume fill

| | 1.5% Dianeal Solution | | | 2.5% Dianeal solution | | | 4.25% Dianeal Solution | | | Extraneal Solution | | |
|---|---|---|---|---|---|---|---|---|---|---|---|---|
| | Dwell | Net UF | Kt/V | Dwell | Net UF | Kt/V | Dwell | Net UF | Kt/V | Dwell | Net UF | Kt/V |
| LA | 2.5 | 37 | | 4.0 | 209 | | 7.0 | 586 | | 16 | 630 | |
| | 7.0 | | .31 | 7.0 | | .35 | 9.0 | | .41 | 16 | | .45 |
| L | 3.5 | 75 | | 6.0 | 335 | | 9.0 | 877 | | 16 | 750 | |
| | 8.0 | | .33 | 9.0 | | .38 | 11.0 | | .48 | 16 | | .47 |

TABLE 11

2500 ml (2.5 L) volume fill

| | 1.5% Dianeal Solution | | | 2.5% Dianeal solution | | | 4.25% Dianeal Solution | | | Extraneal Solution | | |
|---|---|---|---|---|---|---|---|---|---|---|---|---|
| | Dwell | Net UF | Kt/V | Dwell | Net UF | Kt/V | Dwell | Net UF | Kt/V | Dwell | Net UF | Kt/V |
| H | 1.5 | 31 | | 3.0 | 165 | | 4.0 | 457 | | 16 | 739 | |
| | 5.0 | | .41 | 6.0 | | .44 | 7.0 | | .49 | 16 | | .56 |
| HA | 2.0 | 42 | | 4.0 | 222 | | 6.0 | 606 | | 16 | 777 | |
| | 6.0 | | .40 | 7.0 | | .44 | 8.0 | | .50 | 16 | | .59 |
| LA | 3.0 | 47 | | 5.0 | 258 | | 8.0 | 712 | | 16 | 689 | |
| | 8.0 | | .39 | 9.0 | | .43 | 11.0 | | .51 | 16 | | .53 |
| L | 4.0 | 93 | | 7.0 | 408 | | 10.0 | 1065 | | 16 | 825 | |
| | 9.0 | | .42 | 11.0 | | .48 | 13.0 | | .58 | 16 | | .57 |

TABLE 12

3000 ml (3 L) volume fill

| | 1.5% Dianeal Solution | | | 2.5% Dianeal solution | | | 4.25% Dianeal Solution | | | Extraneal Solution | | |
|---|---|---|---|---|---|---|---|---|---|---|---|---|
| | Dwell | Net UF | Kt/V | Dwell | Net UF | Kt/V | Dwell | Net UF | Kt/V | Dwell | Net UF | Kt/V |
| H | 2.0 | 38 | | 3.5 | 197 | | 5.0 | 545 | | 16 | 806 | |
| | 5.0 | | .49 | 7.0 | | .52 | 8.0 | | .59 | 16 | | .65 |
| HA | 2.5 | 52 | | 5.0 | 264 | | 7.0 | 719 | | 16 | 836 | |
| | 7.0 | | .48 | 3.0 | | .52 | 10.0 | | .60 | 16 | | .65 |
| LA | 3.5 | 57 | | 6.0 | 302 | | 9.0 | 839 | | 16 | 730 | |
| | 9.0 | | .47 | 10.0 | | .52 | 12.0 | | .81 | 16 | | .61 |
| L | 5.0 | 112 | | 8.0 | 465 | | 12.0 | 1249 | | 16 | 872 | |
| | 10.0 | | .50 | 12.0 | | .57 | 15.0 | | .70 | 16 | | .66 |

The tables demonstrate that some of the trends discussed above hold true across many variables, e.g., ultrafiltration increases with decreasing transport properties, and ultrafiltration also increases with increasing fill volume. Other trends can also be discerned, but the point remains the same: the data can be used to select a dwell time to optimize the dialysis session for a particular patient, based on the patient's transport properties, fill volume, and dialysis solution used.

It is understood that the tables are simply an easy way to present data. The correspondence between dialysis input parameters, desired therapy outcomes, and dwell times may reside as data in one or more tables, such as look-up tables. The data may also take the form of graphs, or may be reduced to equations. There are many embodiments of the invention, including all of these methods of presenting, storing, and using the data.

Figure 9:
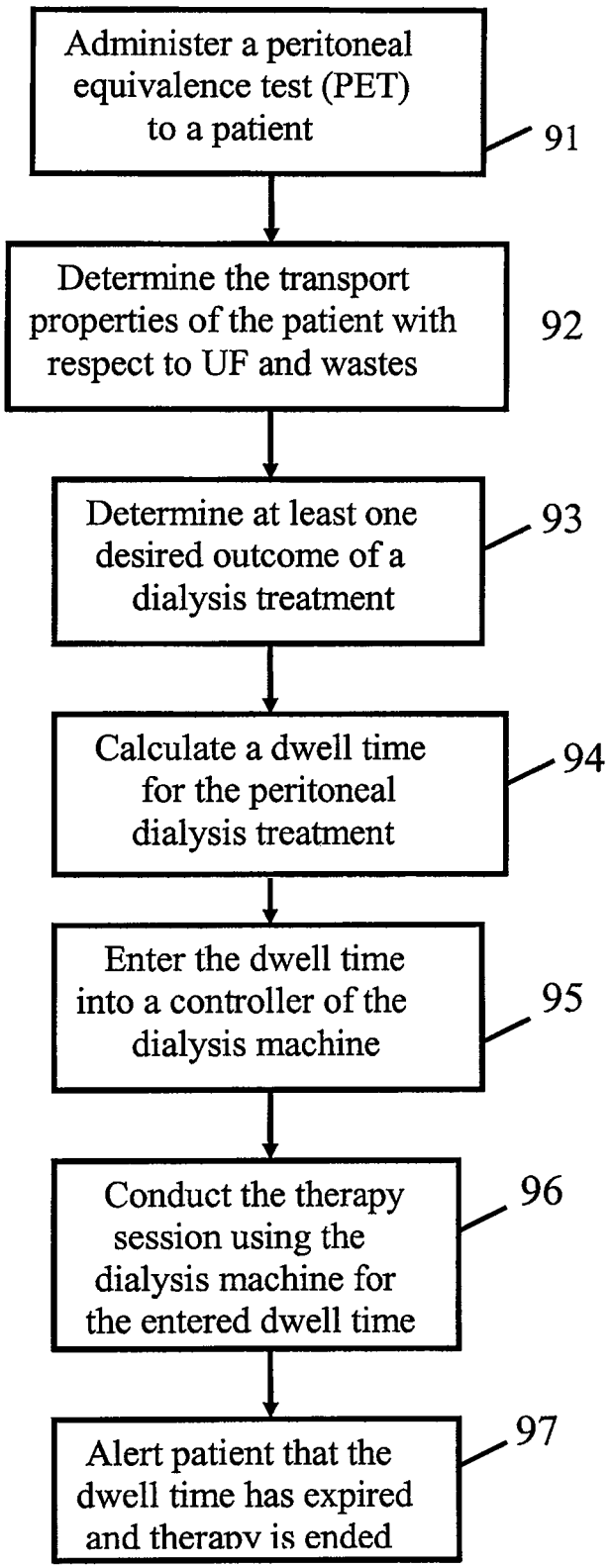
FIG. 9 is a flow chart for a method of determining a dwell time for an optimal therapy outcome.

A flowchart for a method of optimizing a therapy session is depicted in FIG. 9. The classification of the patient as a high transporter, high-average transporter, and so forth, is determined by administering 91 a PET test. In other embodiments, other tests may be used, and other classifications may be used. The point is to determine how each individual patient can benefit from the dialysis conditions best suited for him or her. In any event, the transport properties of the patient with respect to ultrafiltration and waste transport are determined 92. The patient or a caregiver, such as a medical professional, determines 93, e.g., selects, at least one desired outcome of a dialysis treatment, such as ultrafiltrate volume or urea clearance.

A dwell time for optimizing the selected outcome is then calculated or estimated 94. The selected dwell time is then entered 95 into the controller of the dialysis machine. For dialysis treatments that do not necessarily involve a peritoneal dialysis machine, such as ambulatory peritoneal dialysis, the controller may simply be a timer on the transfer set. The therapy session is then conducted 96 using the entered dwell time. At the end of the dwell time, the timer or other alerting device alerts 97 the patient that the dwell time has expired and the therapy session may be ended.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

Smart Patient Transfer Set

In a further embodiment, the present disclosure sets forth a peritoneal dialysis "smart" system and method for performing peritoneal dialysis, which is applicable to both continuous ambulatory peritoneal dialysis ("CAPD") and automated peritoneal dialysis ("APD") therapies. The system and method take advantage of one common component for both CAPD and APD, namely, that both types of systems include or connect to a patient's transfer set. As discussed above, the patient's transfer set is a permanent item worn and carried around by the patient. The set is connected to a tube that transitions to an indwelling catheter located within the patient's peritoneal cavity.

The patient's transfer set connects to a connector located at the end of a patient fill tube. The fill tube can extend from a manual flow control device for CAPD or a disposable cassette for APD. The manual flow control device connects to a single supply bag typically. The disposable cassette connects to multiple supply bags typically. Thus another constant with CAPD and APD systems is the use of at least one supply bag.

The system places a readable identifier on a connector located at the end of a tube or pigtail extending from the supply bag. Alternatively, the identifier is placed on the tube or pigtail itself. Further alternatively, if the bags do not include tubes or pigtails and are instead spiked, the bags themselves may be provided with identifiers that are read. Still further alternatively, in an APD embodiment the identifier can be placed on a connector connected to a patient fill line running from the APD machine. The identifiers in any case can be a barcode or radio frequency identifier, for example.

A reader is provided that reads the identifier. The reader can be integrated into the APD machine or be provided in a standalone unit. It is contemplated to use the standalone unit in both APD and CAPD therapies. The reader reads the identifier, processes the information obtained from the identifier, and sends a signal based on the processed information.

The patient's transfer set receives the signal sent from the reader. The signal may be a wireless signal sent from a transmitter (or transceiver) of the reader to a receiver (or transceiver) of the transfer set. The transceivers are provided alternatively for two-way communication between the reader and the transfer set. The transfer set is also provided with microprocessing and memory that are programmed to act on the received information. The microprocessor outputs to an output device, such as an alarm and/or readout, that communicates information to the patient. In one example, the supply container identifier supplies information regarding the volume of fluid in the supply container and a dextrose or glucose level of the dialysate residing in the container. The identifier may also include expiration date information for the supply.

Figure 10:
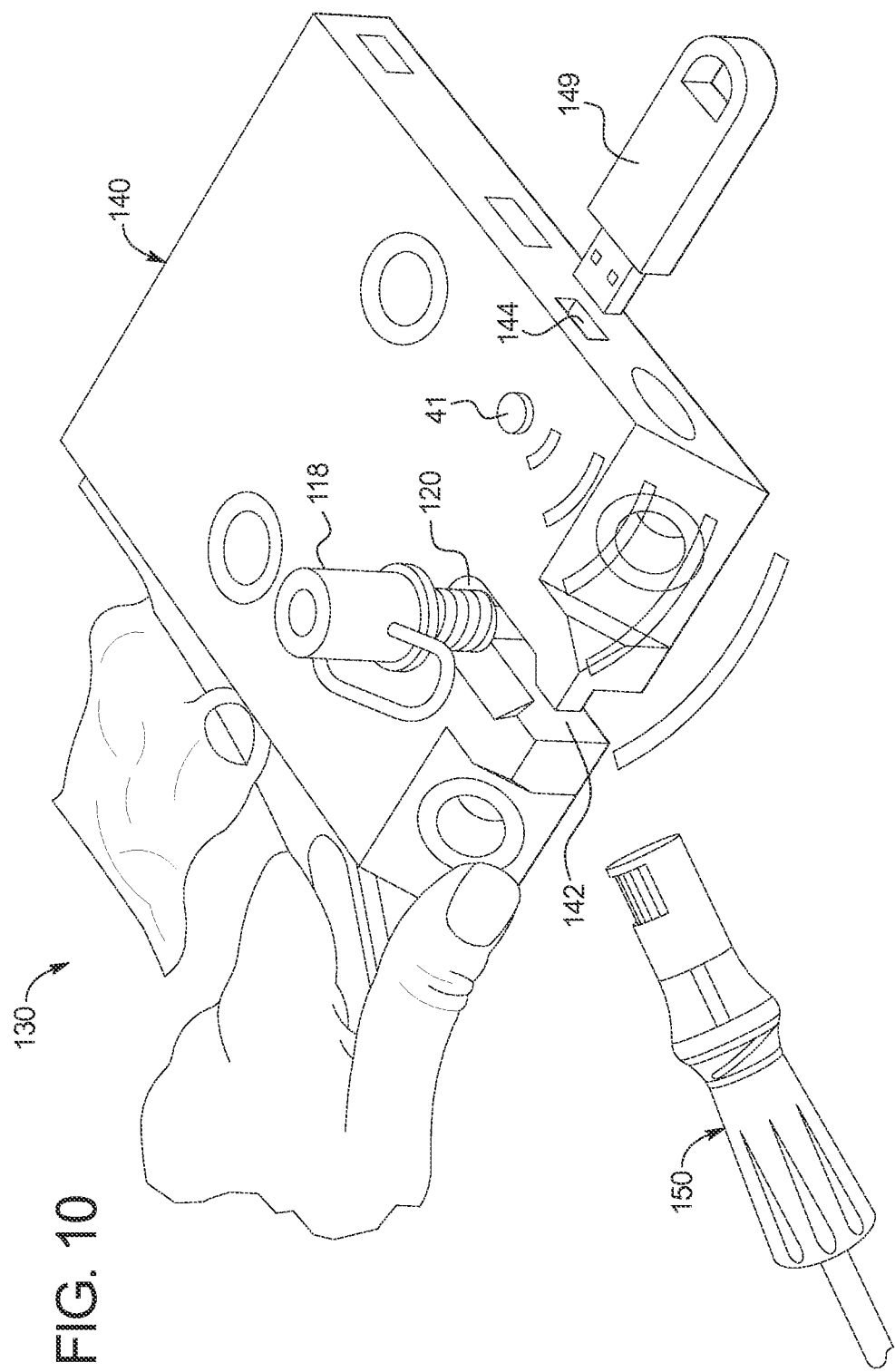
FIG. 10 is a perspective view of an alternative embodiment of the present disclosure, which employs a smart transfer set.

Referring now to FIGS. 10 and 11, one embodiment of a smart transfer set system 130 and corresponding method is illustrated. System 130 includes two primary components, namely, an alternative control portion 140, which is hereafter called a remote docking unit, and an alternative or smart transfer set 150. Remote docking unit 140 can be configured for operation with control portion 30 of the dialysis machine 10 discussed above for APD. Alternatively, docking unit 140 operates solely with smart transfer set 150 to run a CAPD therapy.

Docking unit 140 accepts a supply line connector 118 having a tag or identifier 120, which can be a barcode or radio frequency identification ("RFID") tag. Tag or identifier 120 is placed alternatively on the supply line itself, e.g., near supply line connector 118. Further alternatively, in APD application, supply line connector 118 can instead be a connector for the patient line 18 coming from APD machine 30.

Docking unit 140 includes a reader 147 positioned in suitable proximity to tag or identifier 120 to read the information from the tag. Reader 147 can for example be a barcode scanner that faces barcode 120 to read its information. Reader 147 is alternatively an RFID reader that may not have to be placed as directly adjacent to RFID tag 120 to read the information.

The information in one embodiment includes (i) the volume, (ii) the type and (iii) the expiration date of solution or dialysis fluid held by the supply bag connected to the supply line connected to supply line connector 118. If the dialysis fluid has expired, an alarm will be posted and if used with APD machine 10, system 130 will not allow therapy to continue. The volume and type of dialysis solution is used to set fill and dwell times as discussed in detail below.

Docking unit 140 also includes a memory card or drive port 144, such as a universal serial bus ("USB") port for receiving a memory storage member 149, such as a flash drive or disk drive. The memory storage member 149 stores patient specific data, such as data shown above in Tables 1 to 12, which is combined with data from tag or identifier 120 to determine an optimal dwell time for the patient. In one embodiment, memory storage member 149 needs to be inserted into port 144 for each treatment. In another embodiment, memory storage member 149 needs to be inserted only once into port 144 until the data on the memory storage member 149 is changed.

In one alternative embodiment discussed below in connection with FIG. 13, a separate proximity sensor 148 is provided. Proximity sensor 148 can be a capacitive or inductive proximity sensor. The proximity sensor senses the presence or absence of connector 118 for reasons discussed below.

Each of the reader 147, memory member receiving port 144 and proximity sensor 148 is linked to a controller 42 provided within docking unit 140. In the illustrated embodiment (and for any of the embodiments discussed herein), controller 42 includes processing 42a and memory 42b. Processing 42a and memory 42b are also linked in communication with a wireless transmitter (Tx) or transceiver (Tc) 41, which communicates wirelessly with a receiver (Rx) or transceiver (Tc) 141 located within smart transfer set 150.

Controller 42 also commands one or more output device 45, such as a light and/or buzzer, which can for example communicate to the patient whenever docking unit 140 is processing or transmitting data. For example, an alarm output device 45 can be provided to indicate when that the solution of a bag connected to connector 118 has expired. Output device 45 can alternatively be a display which indicates "expired" in this instance.

A power supply 43, which can be AC sourced, be a rechargeable battery or be a replaceable battery supplies the appropriate power to each of controller 42, output device 45, reader 147, transmitter (Tx) or transceiver (Tc) 41 and proximity switch 148 (if provided). Low power can be indicated to the patient via light indication or via a readout.

Processing 42 and memory 42b receive the solution data from reader 147 and patient data from memory storage member 149 and process the data to arrive at an optimal dwell time according to the methods described herein. That optimal dwell time is then sent via transmitter (Tx) or transceiver (Tc) 41 wirelessly (possibly with other information as discussed below) to receiver (Rx) or transceiver (Tc) 141 located within smart transfer set 150. Alternatively, docking unit 140 serves mainly as an information transfer device, which transfers solution data from reader 147 and patient data from memory storage member 149 to smart transfer set 150, which then uses its processing 142*a* and memory 142*b* to compute the optimal dwell duration (and other needed information as discussed below). It may be possible under one of these scenarios to remove or limit the processing and memory from one of docking unit 140 and smart transfer set 150.

As seen in FIG. 11, smart transfer set 150 includes a controller 142 having processing 142*a* and memory 142*b*, which accept information from receiver (Rx) or transceiver (Tc) 141 and command operation of one or more patient output device, such as a light and/or buzzer 145 and a small (e.g., liquid crystal display ("LCD")) readout 146. In one embodiment, discussed below in connection with FIG. 12, smart transfer set 150 is provided with a patient input device 152, such as a pushbutton or switch. Input device 152 inputs a signal to controller 142, for example, to indicate when a fill of the solution from the bag to the patient has been completed.

Transfer set 150 also includes a power supply 143, which can be a rechargeable battery or a replaceable battery, and which supplies the appropriate power to each of controller 142, receiver (Rx) or transceiver (Tc) 141 and output devices 145 and 146. Again, low power can be indicated to the patient via light indication or via a readout.

Referring now to FIG. 12, a method 160 for operating system 130 is illustrated. Upon beginning method 160 as seen at oval 162, dwell duration is determined as seen at block 164. Dwell duration is calculated using the solution data from reader 147 and patient data from memory storage member 149 and the methodology set forth herein by either the controller 42 of docking unit 140 or controller 142 of smart transfer set 150 as discussed above. Dwell time duration is thus either determined at smart transfer set 150 or sent to smart transfer set 150 from docking unit 140, and in any case is known by smart transfer set 150 at block 164.

At diamond 166, method 160 waits for the patient to press input device 152 indicating that a fill from a supply bag connected to connector 118 has been completed. Method 160 allows for the patient to fill as fast or slow as the patient desires and is independent of fill time. When the patient presses input device 152 indicating that the fill is complete, method 160 proceeds to block 168, at which time the optimal dwell duration beings to run. Small display 146 at FIG. 11 shows one embodiment in which dwell duration is counted backwards from the starting duration down to zero. It is contemplated to build false input device 152 activation protection into method 160, e.g., requiring a confirm press of the input device or allowing a second press of the input device to undue the original input and start over.

At diamond 170, method 160 waits for the dwell duration to run out completely, at which time the patient is alerted that dwell is finished and that the patient should begin to drain the spent dialysate, as seen at block 172. Different scenarios are contemplated. For example, light/buzzer 145 could flash with five or ten minutes before dwell is completed to give the patient a heads-up the he/she needs to get to a place appropriate for draining. All the while clock 146 is counting down to zero. At zero, light/buzzer 145 lights/sounds to indicate that dwell is complete and that drain needs to start as soon as possible. The buzzer can be for a predetermined duration, and input device 152 can be set to stop the buzzer immediately when pressed in case the patient does not want noise.

At oval 174, method 160 ends. Method 160 is then repeated for each supply bag of the therapy.

Referring now to FIG. 13, another method 180 (actually two versions of this methods as discussed below) for operating system 130 is illustrated. Upon beginning method 180 as seen at oval 182, fill and dwell durations are determined as seen at block 184. Dwell duration is again calculated using the solution data from reader 147 and patient data from memory storage member 149 and the methodology set forth herein by either the controller 42 of docking unit 140 or controller 142 of smart transfer set 150 as discussed above. Dwell duration is in any case is known by smart transfer set 150 at block 184. Both fill and dwell durations are affected by the volume of the dialysis solution in the supply container. Dwell duration is also affected by the type or dextrose level of the dialysis solution. Fill duration is also effected by the patient's fill position relative to the supply container if the fill is a gravity fill. Position can play a role even when fluid is pumped from the supply bag to the patient. Thus, the fill duration may be for a particular head height level, which is either known generally by the patient or communicated via system 130 to the patient via the APD machine 10, docking unit 140 or smart transfer set 150.

At block 186*a*, the patient is alerted that the patient should begin filling fresh dialysate from the supply container, through connector 118 and transfer set 150, to the patient's peritoneum. Different scenarios are contemplated for the fill duration run-out indicated at block 188. For example, light/buzzer 145 could flash and or buzz, while display 146 counts the fill duration down to zero. Display 146 could also display the word "fill" to indicate that the current countdown is for filling. Alternatively or additionally, light 145 could be lighted a different color for fill (e.g., green) and dwell (e.g., yellow).

At diamond 190, method 180 waits for the fill duration to run out completely, at which time the patient is alerted that fill is supposed to be finished and that the dwell duration is beginning. Different scenarios are contemplated dwell duration run-out indicated at block 192. For example, light/buzzer 145 could flash and or buzz for a period to indicate the transition from fill to drain, while display 146 resets itself and counts now the dwell duration down to zero. Display 146 could also display the word "dwell" to indicate that the current countdown is for filling. Alternatively or additionally, light 145 could be changed from, e.g., green to yellow. Method 180 accordingly does not require input device 152 because the method transitions automatically from fill to dwell.

At diamond 190, method 180 waits for the dwell duration to run out completely, at which time the patient is alerted that dwell is finished and that the patient should begin to drain the spent dialysate, as seen at block 198. As with method 160, impending dwell completion can be indicated by the flashing of light/buzzer 145 with five or ten minutes before dwell is done to give the patient a heads-up the he/she needs to get to a place appropriate for draining. All the while clock 146 is counting down to zero. At zero, light/buzzer 145 lights/sounds to indicate that dwell is complete and that drain needs to start as soon as possible. The buzzer can be again be for a predetermined duration, and input device 152 can be set to stop the buzzer immediately when pressed in case the patient does not want noise.

Block 186*b* illustrates a modification of method 180. If there is going to be a substantial error in estimating fill duration, it is likely going to involve an instance in which system 130 assumes the patient is diligently following the time runouts to meet the deadlines or time expirations. It may occur however that the patient becomes distracted or forgets that the fill time is underway. In either case, it is likely that the patient will have left connector 118 positioned in its holding port of docking unit 140. The modification via block 186b assumes that once the patient has undertaken to remove connector 118 from docking unit 140, that the patient will thereafter diligently connect connector 118 to the transfer set for filling. Here, proximity sensor 148 senses a removal of connector 118 from the docking unit, sends a signal to controller 42, which commands Tx/Tc 41 to send a corresponding wireless signal to Rx/Tc 141 of transfer set 150, which is routed to controller 142, which then initiates the fill duration run-out sequence indicated at block 188. If space permits, proximity sensor 148 can be located alternatively in transfer set 150, which then looks for the presence of connector 118 to begin the fill duration run-out. In either case, method 180 is immune to patient delay in removing connector 118 from docking unit 140.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method for accomplishing automated peritoneal dialysis, comprising:
   administering a peritoneal equilibration test ("PET") to a patient;
   determining and recording a patient status as a result of the PET test, the patient status selected from the group consisting of a high transporter, average transporter, low transporter, and combinations thereof;
   calculating a peritoneal dialysis dwell time based on the patient status and at least one peritoneal dialysis therapy outcome, wherein the dwell time optimizes the at least one peritoneal dialysis therapy outcome for the patient, said calculating including (i) averaging an optimized dwell time for a plurality of peritoneal dialysis therapy outcomes or (ii) using a weighted average of an optimized dwell time of each of the plurality of dialysis therapy outcomes; and
   performing at least one treatment cycle with the calculated peritoneal dialysis dwell time using an automated peritoneal dialysis machine.

2. The method of claim 1, wherein the step of calculating is based on a plurality of peritoneal dialysis input parameters.

3. The method of claim 1, further comprising storing a database of peritoneal dialysis dwell times, peritoneal dialysis input parameter values and peritoneal dialysis therapy outcomes in a memory of a computer or in a memory accessible to the computer for carrying out the step of calculating.

4. The method of claim 1, wherein the at least one peritoneal dialysis therapy outcome is selected from the group consisting of: a net ultrafiltrate volume, a net ultrafiltrate volume rate, an absorption of carbohydrates from a peritoneal dialysis fluid, a phosphate removal, a creatinine clearance, and a urea clearance.

5. The method of claim 1, wherein the step of calculating is also based on a composition of a peritoneal dialysis fluid and a peritoneum fill volume.

6. The method of claim 1, further comprising infusing a peritoneal dialysis fluid into a peritoneum of the patient; and notifying the patient when the dwell time has elapsed.

7. A method for accomplishing automated peritoneal dialysis, comprising:
   determining peritoneal transport properties of a patient;
   determining a classification of the peritoneal transport properties of the patient;
   calculating a peritoneal dialysis dwell time based on the classification, a plurality of peritoneal dialysis input parameters, and at least one desired peritoneal dialysis therapy outcome, wherein the dwell time is calculated to maximize the at least one desired peritoneal dialysis therapy outcome, said calculating including (i) averaging an optimized dwell time for a plurality of peritoneal dialysis therapy outcomes or (ii) using a weighted average of an optimized dwell time of each of the plurality of peritoneal dialysis therapy outcomes; and
   performing at least one treatment cycle with the calculated peritoneal dialysis dwell time using an automated peritoneal dialysis machine.

8. The method of claim 7, further comprising storing data of a correspondence between the plurality of peritoneal dialysis input parameters, a plurality of therapy outcomes, and values of a peritoneal dialysis dwell time in a memory of a computer or in a memory accessible to the computer for carrying out the step of calculating.

9. The method of claim 7, wherein the at least one desired peritoneal dialysis outcome is selected from the group consisting of: a net ultrafiltrate volume, a net ultrafiltrate volume rate, a reduction in absorption of carbohydrates from a peritoneal dialysis fluid, a urea clearance, a sodium clearance, a middle molecule clearance, and a creatinine clearance.

10. The method of claim 7, wherein the step of calculating is based on a body surface area or a total body water volume of a patient.

11. The method of claim 7, further comprising infusing a peritoneal dialysis fluid into a peritoneum of the patient;
   notifying the patient when the dwell time has elapsed; and
   removing the peritoneal dialysis fluid from the peritoneum after the dwell time.

12. A system for calculating a peritoneal dialysis dwell time and conducting automated peritoneal dialysis, the system comprising:
   a processor for operating an automated peritoneal dialysis machine;
   a memory of the processor or a memory accessible to the processor, the memory storing a look-up table containing peritoneal dialysis input parameters, peritoneal dialysis therapy outcomes, and peritoneal dialysis dwell times corresponding to the input parameters and dwell times; and
   a software program stored in the memory of the processor or the memory accessible to the processor for receiving a selection or an input of at least one desired therapy outcome of a patient and calculating a dwell time for the patient for optimizing the at least one peritoneal dialysis therapy outcome for the patient, wherein the dwell time is calculated by (i) averaging an optimized dwell time for a plurality of peritoneal dialysis therapy outcomes or (ii) using a weighted average of an optimized dwell time of each of the plurality of peritoneal dialysis therapy outcomes.

13. The system of claim 12, wherein the plurality of peritoneal dialysis therapy outcomes include at least two of a net ultrafiltrate volume, an absorption of carbohydrates, a urea clearance, a phosphate clearance, and a creatinine clearance.

14. The system of claim 12, wherein the look-up table includes input parameters based on transport properties of the patient, a composition of a peritoneal dialysis fluid, and a peritoneum fill volume, and optionally, a body surface area of the patient or a total body volume of the patient.

15. The system of claim 12, further comprising a housing for the computer system and an input device for inputting at least one peritoneal dialysis input parameter, a composition of a peritoneal dialysis fluid, and inputting or selecting the at least one dialysis therapy outcome.

16. The system of claim 12, further comprising a remote device in communication with the computer system, the remote device including an output device for indicating an end of the dwell time or a time remaining of the dwell time.

17. The system of claim 12, further comprising a patient transfer set, including an output device for indicating an end of the dwell time or a time remaining of the dwell time.

18. The system of claim 12, further comprising a peritoneal dialysis machine, wherein the processor forms part of a control system of the peritoneal dialysis machine.

19. A computer program embodied on a computer readable medium for calculating a peritoneal dialysis dwell time, comprising:
a code segment for accessing data of a correspondence between a plurality of peritoneal dialysis input parameters, a plurality of peritoneal dialysis therapy outcomes, and a plurality of peritoneal dialysis dwell times;
a code segment that allows a user to input or to select at least one peritoneal dialysis input parameter from the plurality of peritoneal dialysis input parameters and at least one desired therapy outcome;
a code segment that receives an indication of the at least one input parameter and at least one desired therapy outcome selected by the user;
a code segment that calculates a dwell time corresponding to the at least one desired therapy outcome selected by the user, said code configured to calculate the dwell time by (i) averaging an optimized dwell time for a plurality of peritoneal dialysis therapy outcomes or (ii) using a weighted average of an optimized dwell time of each of the plurality of peritoneal dialysis therapy outcomes; and
a code segment that inputs the dwell time to an automated peritoneal dialysis machine.

20. The computer program according to claim 19 wherein the at least one desired therapy outcome is selected from the group consisting of: a net ultrafiltrate volume, a net ultrafiltrate volume rate, an absorption of carbohydrates from a peritoneal dialysis fluid, a urea clearance, and a creatinine clearance.

21. The computer program according to claim 19, further comprising the data, said data stored on the computer-readable medium or in a memory accessible by the computer readable medium as a look-up table or as one or more formulae that express the correspondence.

22. An automated peritoneal dialysis system, comprising:
a dialysis cassette and a housing suitable for receiving the cassette, the cassette including at least one pump for pumping dialysis fluid to and from a patient;
a microcontroller suitable for operating the automated peritoneal dialysis system;
a memory of the microcontroller or accessible to the microcontroller, the memory including data of a plurality of dialysis input parameters, a plurality of dialysis dwell times, and a plurality of therapy outcomes corresponding to the input parameters and dwell times, wherein a user instructs the microcontroller to select or calculate a dwell time for optimizing at least one dialysis outcome for a patient; and
a patient transfer device connected to a patient access device, the patient transfer device including electronics in communication with the microcontroller.

* * * * *